United States Patent [19]

Sturm et al.

[11] Patent Number: 4,762,830
[45] Date of Patent: Aug. 9, 1988

[54] 5-(AZOLYLOXYPHENYLCARBAMOYL)-BARBITURIC ACID DERIVATIVES AS ANTHELMINTICS

[75] Inventors: Elmar Sturm, Aesch; Jean J. Gallay, Magden; Haukur Kristinsson, Basel, all of Switzerland; Georg Pissiotas, Lörrach, Fed. Rep. of Germany

[73] Assignee: Ciba-Geigy Corporation, Ardsley, N.Y.

[21] Appl. No.: 830,430

[22] Filed: Feb. 13, 1986

[30] Foreign Application Priority Data

Feb. 15, 1985 [CH] Switzerland .................. 705/85

[51] Int. Cl.[4] .............. A61K 31/505; C07D 403/10; C07D 403/12
[52] U.S. Cl. .................... 514/270; 544/300
[58] Field of Search .................. 544/300; 514/270

[56] References Cited

U.S. PATENT DOCUMENTS

| 3,679,695 | 7/1972 | Moore | 548/186 |
|---|---|---|---|
| 3,961,061 | 6/1976 | Kramer et al. | 544/301 |
| 4,005,202 | 1/1977 | Beard | 514/269 |
| 4,239,762 | 12/1980 | Kramer et al. | 424/254 |
| 4,283,444 | 8/1981 | De Sousa et al. | 544/300 |
| 4,399,280 | 8/1983 | De Sousa et al. | 544/301 |
| 4,602,912 | 7/1986 | De Sousa et al. | 544/300 |

FOREIGN PATENT DOCUMENTS

| 7541 | 2/1980 | European Pat. Off. | 514/270 |
|---|---|---|---|
| 105029 | 4/1984 | European Pat. Off. | 544/300 |
| 167491 | 1/1986 | European Pat. Off. | 544/300 |
| 2225071 | 3/1972 | Fed. Rep. of Germany . | |
| 2641979 | 5/1977 | Fed. Rep. of Germany . | |
| 2719777 | 11/1977 | Fed. Rep. of Germany . | |
| 2936457 | 3/1980 | Fed. Rep. of Germany . | |
| 3238079 | 4/1984 | Fed. Rep. of Germany . | |
| 2126582 | 3/1984 | United Kingdom | 514/270 |
| 2145087 | 3/1985 | United Kingdom | 514/270 |
| 2152047 | 7/1985 | United Kingdom | 514/270 |
| 2171099 | 8/1986 | United Kingdom | 514/270 |

OTHER PUBLICATIONS

Burckhardt et al, CA 103-178271x.
Kuehne et al, CA 105-60628g.
C.A. 99: 72077x, De Sousa et al. (1983).
C. A. 79: 126394f, Nagai et al. (1973).
Excerpt-EP Search Report.

Primary Examiner—Donald G. Daus
Assistant Examiner—Cecilia Shen
Attorney, Agent, or Firm—Meredith C. Findlay; Edward McC. Roberts

[57] ABSTRACT

The invention relates to novel 5-(azolyloxyphenylcarbamoyl)barbituric acid derivatives of the general formula I

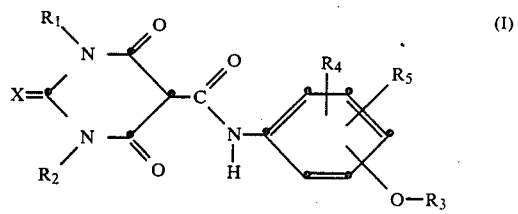

wherein
X is oxygen or sulfur;
$R_1$ is $C_1$-$C_6$alkyl, $C_1$-$C_6$alkoxy, $C_3$-$C_6$cycloalkyl or allyl;
$R_2$ is $C_1$-$C_6$alkyl or allyl;
$R_3$ is an unsubstituted or substituted five-membered azole ring which is bound through carbon and is selected from the group consisting of benzimadazole, benzoxazole, benzothiazole, imidazole, oxazole, thiazole, oxadiazole, thiadiazole and triazole; and
$R_4$ and $R_5$ are each independently of the other hydrogen, $C_1$-$C_6$alkyl, $C_1$-$C_6$haloalkyl, $C_1$-$C_6$alkoxy or $C_1$-$C_6$haloalkoxy;

and to the tautomers and salts thereof, as anthelmintic compounds. Together with suitable carriers and further assistants, these compounds may be used in particular for controlling helminths which are parasites of animals.

22 Claims, No Drawings

5-(AZOLYLOXYPHENYLCARBAMOYL)BARBITURIC ACID DERIVATIVES AS ANTHELMINTICS

The present invention relates to novel substituted 5-(azolyloxyphenylcarbamoyl)barbituric acid derivatives having anthelmintic activity, to compositions containing these compounds as active ingredients, and to the use of said compounds or compositions for controlling helminths, in particular nematodes, cestodes and trematodes in domestic animals and productive livestock, especially in mammals. The invention further relates to the preparation of the novel compounds and of compositions containing them.

Specifically, the present invention relates to novel compounds of the general formula I

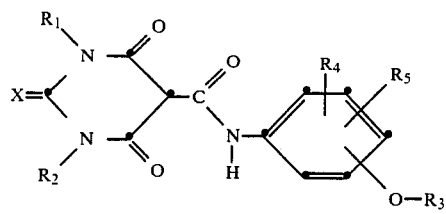

wherein

X is oxygen or sulfur;

$R_1$ is $C_1$–$C_6$alkyl, $C_1$–$C_6$alkoxy, $C_3$–$C_6$cycloalkyl or allyl;

$R_2$ is $C_1$–$C_6$alkyl or allyl;

$R_3$ is an unsubstituted or substituted five-membered azole ring which is bound through carbon and is selected from the group consisting of benzimidazole, benzoxazole, benzothiazole, imidazole, oxazole, thiazole, oxadiazole, thiadiazole and triazole; and $R_4$ and $R_5$ are each independently of the other hydrogen, $C_1$–$C_6$alkyl, $C_1$–$C_6$haloalkyl, $C_1$–$C_6$alkoxy or $C_1$–$C_6$haloalkoxy; and to the tautomers and salts thereof.

The compounds of formula I may exist for example in the following tautomeric forms:

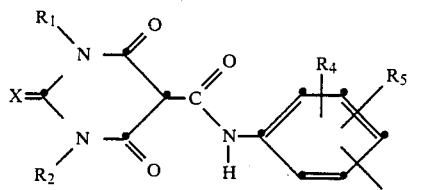

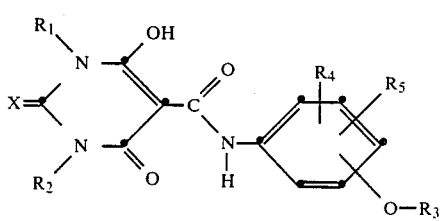

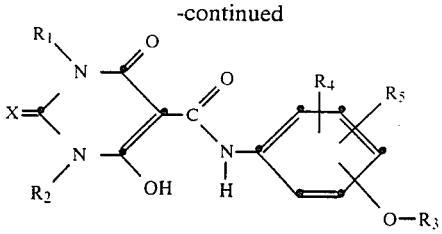

The invention relates to all tautomeric forms of the compounds of formula I.

The five-membered azole ring $R_3$ is thus always bound through a carbon atom to the phenolic oxygen atom of the molecule and may itself in turn be unsubstituted or substituted. Compounds of formula I, wherein $R_3$ has for example one of the meanings indicated below, form one of the following preferred groups a to f of the invention depending on the respective definition of $R_3$:

| Group | $R_3$ | Type |
|---|---|---|
| (a) | (structure) | benzimidazol-2-yl<br>benzoxazol-2-yl<br>benzothiazol-2-yl |
| (b) | (structure) | imidazol-2-yl<br>oxazol-2-yl<br>thiazol-2-yl |
| (c) | (structure) | [1H–1,2,4-triazol]-5-yl<br>[1,2,4-oxadiazol]-5-yl<br>[1,2,4-thiadiazol]-5-yl<br>[1,2,4-oxadiazol]-3-yl<br>[1,2,4-thiadiazol]-3-yl |
| (d) | (structure) | [1H–1,2,4-triazol]-3-yl |
| (e) | (structure) | [1,3,4-oxadiazol]-2-yl<br>[1,3,4-thiadiazol]-2-yl<br>[4H–1,2,4-triazol]-5-yl |
| (f) | (structure) | [1H–1,2,4-triazol]-5-yl | in which formulae

Y is oxygen, sulfur or $NR_{10}$;

Z is oxygen, sulfur or NH;

$R_6$ and $R_7$ are each independently of the other hydrogen, $C_1$–$C_4$alkyl, $C_1$–$C_4$haloalkyl, $C_1$–$C_4$alkoxy, $C_1$–$C_4$haloalkoxy, $C_1$–$C_4$alkylthio, halogen, nitro or cyano;

$R_8$ and $R_9$ are each independently of the other hydrogen, $C_1$–$C_6$alkyl, $C_3$–$C_7$cycloalkyl, $C_1$–$C_6$haloalkyl, $C_1$–$C_6$alkoxy, $C_1$–$C_6$alkylthio, halogen or nitro;

$R_{10}$ is hydrogen or $C_1$–$C_6$alkyl; and $R_{11}$ is $C_1$–$C_6$alkyl.

Within groups b to f, those compounds of formula I are interesting wherein Y, Z, $R_{10}$ and $R_{11}$ are as defined above and each of $R_8$ and $R_9$ independently of the other is $C_3$–$C_7$cycloalkyl, preferably cyclopropyl or cyclohexyl, which is unsubstituted or substituted by halogen or $C_1$–$C_3$alkyl.

Thus the substituent $R_3$ has, inter alia, the following meanings:

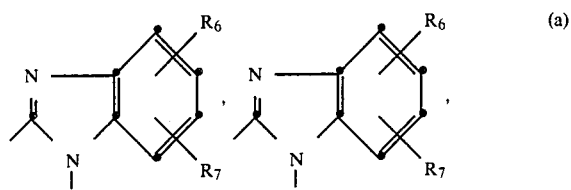 (a)

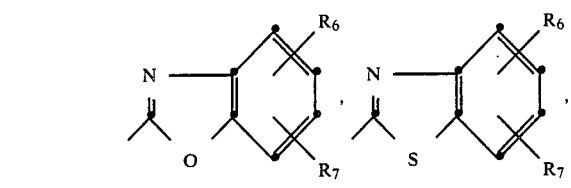

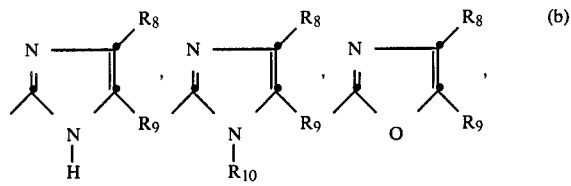 (b)

 (c)

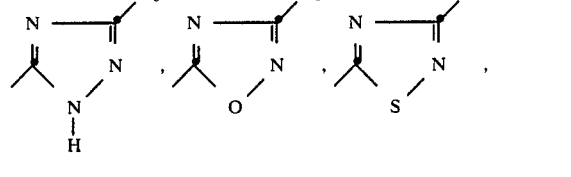

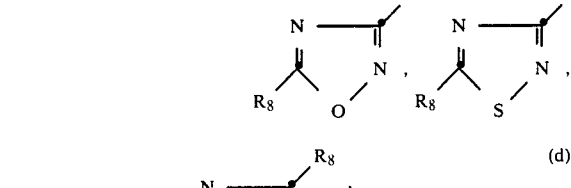 (d)

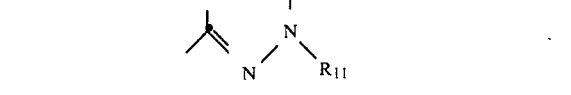

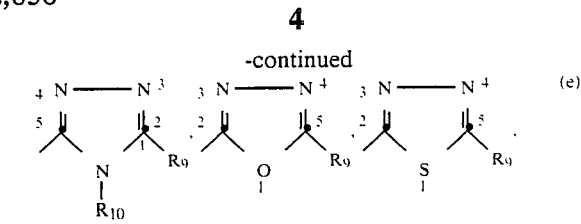 (e)

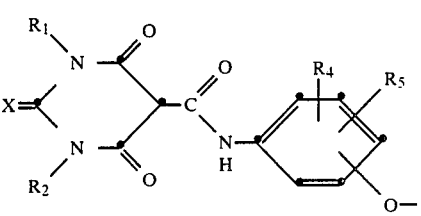 (f)

in which formulae the substituents $R_6$ to $R_{11}$ are as defined above.

Preferred are all groups of compounds of formula I which are formed by combination of the molecule fragment wherein X, $R_1$, $R_2$, $R_4$ and $R_5$ are as defined for formula I, with an azole $R_3$ as indicated under a to f. Each of these groups constitutes an object of the present invention.

Within these groups, those compounds of formula I are preferred wherein $R_1$ is methyl or methoxy; $R_2$ is methyl; and each of $R_4$ and $R_5$ independently of the other is hydrogen, methyl, $CF_3$, $OCH_3$, $OCHF_2$ or $OCF_3$.

Within group Ia, those compounds of formula I are additionally preferred wherein each of $R_6$ and $R_7$ independently of the other is hydrogen, methyl, $CF_3$, methoxy, halomethoxy, fluorine, chlorine or bromine and the remaining substituents are as defined above.

Within groups Ib to If, those compounds of formula I are additionally preferred wherein each of $R_8$ and $R_9$ independently of the other is hydrogen, methyl, ethyl, $C_3$–$C_7$cycloalkyl, $CF_3$, $C_2F_5$, $C_3F_7$, $CCl_3$, $CHCl_2$, $CH_2Cl$, $SCH_3$ or halogen; $R_{10}$ is hydrogen or methyl; and $R_{11}$ is $C_1$–$C_4$alkyl, preferably methyl.

Depending on the number of carbon atoms indicated, within the scope of this invention alkyl by itself or as moiety of another substituent will be understood as meaning for example the following groups: methyl, ethyl, butyl, pentyl or hexyl, as well as the isomers thereof, e.g. isopropyl, isobutyl, sec-butyl, tert-butyl, isopentyl. Halogen-substituted alkyl (haloalkyl) by itself or as moiety of haloalkoxy is a mono- to perhalogenated alkyl substituent, e.g. $CHCl_2$, $CH_2Cl$, $CCl_3$, $CF_3$, $C_2F_5$, $CH_2CH_2Cl$, $C_2Cl_5$, $CHFCHCl_2$, $CF_2H$, with $CF_3$ being preferred. Throughout this specification, halogen will be understood as meaning fluorine, chlorine, bromine or iodine, with fluorine, chlorine or bromine being preferred and chlorine being most preferred. Cycloalkyl is cyclopropyl, cyclobutyl, cyclopentyl or cyclohexyl.

Preferred individual substances are:
1,3-dimethyl-5-[4-(6-bromobenzothiazol-2-yloxy)-phenylcarbamoyl]barbituric acid (1.8);

1,3-dimethyl-5-[4-(6-chlorobenzothiazol-2-yloxy)-phenylcarbamoyl]barbituric acid (1.5);

1,3-dimethyl-5-[4-(6-fluoro(benzothiazol-2-yloxy)-phenylcarbamoyl]barbituric acid (1.38);

1,3-dimethyl-5-[4-(3-dichloromethyl-1,2,4-thiadiazol-5-yloxy)phenylcarbamoyl]barbituric acid (3.1);

1,3-dimethyl-5-[4-(5-tert-butyl-1,3,4-oxadiazol-2-yloxy)phenylcarbamoyl]barbituric acid (4.1);

1,3-dimethyl-5-[4-(5-tert-butyl-1,3,4-thiadiazol-2-yloxy)phenylcarbamoyl]barbituric acid (4.2);

1-methyl-3-methoxy-5-[4-(5-tert-butyl-1,3,4-thiadiazol-2-yloxy)phenylcarbamoyl]barbituric acid (4.55);

1,3-dimethyl-5-[4-(5-isopropyl-1,3,4-oxadiazol-2-yloxy)phenylcarbamoyl]barbituric acid (4.10);

1,3-dimethyl-5-[4-(1-isopropyl-3-trifluoromethyl-1H-1,2,4-triazol-5-yloxy)phenylcarbamoyl]barbituric acid (5.2);

1,3-dimethyl-5-[2,6-dimethyl-4-(1-methyl-3-heptafluoropropyl-1H-1,2,4-triazol-5-yloxy)phenylcarbamoyl]barbituric acid (5.28);

1,3-dimethyl-5-[4-(1-isopropyl-3-pentafluoroethyl-1H-1,2,4-triazol-5-yloxy)phenylcarbamoyl]barbituric acid (5.6);

1,3-dimethyl-5-[4-(1-isopropyl-3-trifluoromethyl-1H-1,2,4-triazol-5-yloxy)-2,6-dimethylphenylcarbamoyl]-barbituric acid (5.5);

1,3-dimethyl-5-[3-(1-methyl-3-trifluoromethyl-1H-1,2,4-triazol-5-yloxy)phenylcarbamoyl]barbituric acid (5.16);

1,3-dimethyl-5-[4-(6-trifluoromethylbenzothiazol-2-yloxy)phenylcarbamoyl]barbituric acid (1.39);

1,3-dimethyl-5-[3-methoxy-4-(5-tert-butyl-1,3,4-thiadiazol-2-yloxy)phenylcarbamoyl]barbituric acid (4.54);

1,3-dimethyl-5-[3-methoxy-4-(6-chlorobenzothiazol-2-yloxy)phenylcarbamoyl]barbituric acid (1.11);

1,3-dimethyl-5-[4-(5,6-dichlorobenzothiazol-2-yloxy)-phenylcarbamoyl]barbituric acid (1.9);

1,3-dimethyl-5-[4-(6,7-dichlorobenzothiazol-2-yloxy)-phenylcarbamoyl]barbituric acid (1.9);

1,3-dimethyl-5-[4-(benzothiazol-2-yloxy)phenylcarbamoyl]barbituric acid (1.32);

1,3-dimethyl-5-[4-(5-chloro-6-fluorobenzothiazol-2-yloxy)phenylcarbamoyl]barbituric acid (1.43);

1,3-dimethyl-5-[4-(7-chloro-6-fluorobenzothiazol-2-yloxy)phenylcarbamoyl]barbituric acid (1.43);

1,3-dimethyl-5-[4-(6-trifluoromethoxybenzothiazol-2-yloxy)phenylcarbamoyl]barbituric acid (1.41);

1,3-dimethyl-5-[2-isopropyl-4-(5-cyclopropyl-1,3,4-oxadiazol-2-yloxy)phenylcarbamoyl]barbituric acid (4.59);

1,3-dimethyl-5-[4-(5-cyclohexyl-1,3,4-thiadiazol-2-yloxy)phenylcarbamoyl]barbituric acid (4.66);

1,3-dimethyl-5-[4-(1-methyl-3-pentafluoroethyl-1H-1,2,4-triazol-5-yloxy)phenylcarbamoyl]barbituric acid (5.37);

1,3-dimethyl-5-[4-(6-methoxybenzothiazol-2-yloxy)-phenylcarbamoyl]barbituric acid (1.40);

1,3-dimethyl-5-[4-(5-cyclopropyl-1,3,4-thiadiazol-2-yloxy)phenylcarbamoyl]barbituric acid (4.69);

1,3-Dimethyl-5-[4-(6-chloro-7-fluorobenzothiazol-2-yloxy)phenylcarbamoyl]barbituric acid (1.78);

1-methyl-3-methoxy-5-[4-(6-chloro-7-fluorobenzothiazol-2-yloxy)phenylcarbamoyl]barbituric acid (1.79);

1,3-dimethyl-5-[3-methoxy-4-(6-chloro-7-fluorobenzothiazol-2-yloxy)phenylcarbamoyl]barbituric acid (1.80).

The salts of compounds of formula I comprise for example the metal, ammonium or amine salts, with the sodium, potassium, aluminium, ammonium or alkylamine salts being preferred. Preferred alkylamine salts are triethylamine salts.

Surprisingly, it has been found that the novel compounds of formula I possess a very favourable activity spectrum against helminths parasitising in the animal organism, in particular in warm-blooded animals and mammals. The novel compounds can be used very successfully in particular against nematodes and at a higher dose also against cestodes and trematodes. A particular feature of the novel compounds is that they are fully effective also against benzimidazole-resistant species, especially against thiabendazole-resistant species. "Thiabendazole" shall be understood as meaning the compound 2-[4-thiazolyl]benzimidazole.

The compounds of formula I are prepared by (a) reacting an ester of formula II

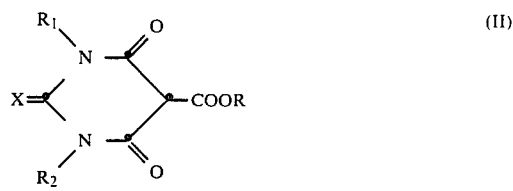 (II)

with an aniline derivative of formula III

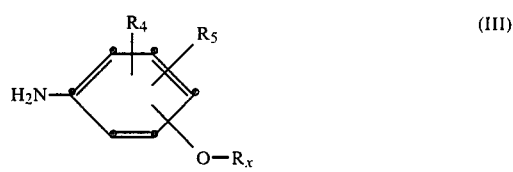 (III)

wherein R is a lower alkyl group or a phenyl group which is unsubstituted or substituted by nitro, or (b) reacting a substituted barbituric acid of formula IV

 (IV)

with a substituted phenylisocyanate of formula V

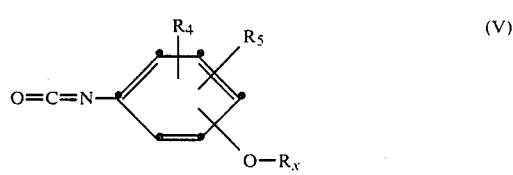 (V)

or (c) reacting a substituted barbituric acid of formula IV with a substituted benzoylazide of formula VI

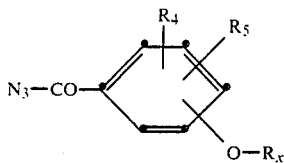

in which formulae II to VI the substituents X, $R_1$, $R_2$, $R_4$ and $R_5$ are as defined for formula I and $R_x$ is hydrogen or a radical as defined for $R_3$, and, in those cases in which $R_x$ is hydrogen, at the starting material stage, one of the hydroxy derivatives ($R_x$=H) of the formula III, V or VI is etherified with a compound of formula XX

wherein Q is a customary leaving group, and the etherified product is then allowed to react further to give the final product, or the hydroxy derivative of formula III, V or VI is first reacted with one of the compounds II or IV to give a hydroxy derivative ($R_1$=H) of formula I', wherein X, $R_1$, $R_2$, $R_4$ and $R_5$ are as defined for formula I and $R_x$ is hydrogen, and then said hydroxy derivative of formula I' is etherified with the compound of formula XX.

Said etherification can thus be carried out either at the starting material stage or at the intermediate stage I' immediately following thereon.

Q in formula XX is either one of the customary leaving groups, e.g. halogen, preferably chlorine, bromine or iodine; a sulfonyloxy group, preferably benzenesulfonyloxy, paratosyloxy or lower alkylsulfonyloxy, preferably mesyloxy; or an acyloxy group such as trifluoroacetyloxy. Q is also a hydroxy group or, in accordance with "Synthesis" 1979, pp. 561–569, a radical

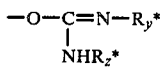

wherein $R_y^*$ and $R_z^*$ are organyl radicals, preferably lower alkyl or unsubstituted or substituted phenyl radicals.

Variants (a) and (c) are carried out at reaction temperatures in the range from 50° to 250° C., preferably from 70° to 220° C. Variant (b) requires temperatures in the range from 0° to 220° C., preferably from 0° to 200° C. The etherification takes place at reaction temperatures in the range from 50° to 150° C., preferably from 80° to 120° C., in an inert solvent or diluent. Reactions (a), (b) and (c) can be carried out under normal or increased pressure and in the absence or, preferably, presence of an inert solvent or diluent. In some cases the reactions are advantageously carried out in the presence of a base.

The salts of compounds of formula I are prepared by conventional neutralisation of the free acid with a base, in particular a physiologically acceptable base. Preferred salts are alkali metal salts such as sodium, potassium or lithium salts, as well as ammonium salts and trialkylamine salts, e.g. the preferred triethylamine salt. Neutralisation is effected in an inert polar solvent, e.g. an alkanol, an ester or an ethereal compound.

Examples of suitable solvents for the preparation of the compounds of the invention are ethers and ethereal compounds such as dialkyl ethers (diethyl ether, diisopropyl ether, tert-butylmethyl ether etc.), anisole, dioxane, tetrahydrofuran; aliphatic and aromatic hydrocarbons such as benzene, toluene, petroleum ether; halogenated hydrocarbons such as chlorobenzene, methylene chloride, chloroform, ethylene chloride, carbon tetrachloride, tetrachloroethylene; nitriles such as acetonitrile and propionitrile; N,N-dialkylated amides such as dimethylformamide; dimethyl sulfoxide; ketones such as acetone, diethyl ketone and methyl ethyl ketone; as well as, in paticular for the etherification reaction, water and alcohols such as methanol, ethanol, isopropanol or butanol; and in general mixtures of such solvents with each other.

Suitable bases are organic and inorganic bases, e.g. preferably tertiary amines such as trialkylamines (trimethylamine, triethylamine, tripropylamine etc.), pyridine and pyridine bases (e.g. 4-dimethylaminopyridine, 4-pyrrolidylaminopyridine etc.), picolines and lutidines, as well as oxides, hydroxides, carbonates and bicarbonates of alkali metals and alkaline earth metals (e.g. CaO, BaO, NaOH, KOH, $Ca(OH)_2$, $KHCO_3$, $NaHCO_3$, $Ca(HCO_3)_2$, $K_2CO_3$, $Na_2CO_3$ etc.), and also acetates such as $CH_3COONa$ or $CH_3COOK$. Further suitable bases are alkali metal alcoholates, e.g. sodium ethylate, sodium propylate, potassium tert-butylate or sodium methylate. For variants (a), (b) and (c) it is advantageous to add the base in 10 to 100% of the equimolar amount and for the etherification reaction in 200% of the equimolar amount, based on the reactants.

In some cases it may be of advantage to carry out the reaction in an inert gas atmosphere. Suitable inert gases are e.g. nitrogen, helium, argon or carbon dioxide.

Compounds of formula III, wherein $R_x$ has the meanings indicated for $R_3$ under formula I, are novel and can be prepared from the corresponding hydroxyanilines of formula III, wherein $R_x$ is hydrogen, by etherification with compounds of formula XX. Said etherification reaction is carried out as described above. However, in place of the hydroxyanilines, the corresponding nitrophenols may be employed, in which case the nitro group has to be reduced in a subsequent reaction to the amino group. Throughout this specification, these compounds ($R_x$=$R_3$) shall be referred to as intermediates of formula III'. Said compounds of formula III' are intermediates which have been specially developed for the preparation of the valuable compounds of formula I. On account of their structural properties, they can be converted [cf. variant (a)] in simple manner into compounds of formula I and constitute therefore an object of this invention. Thus specifically, said compounds are compounds of formula III'

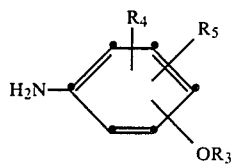

wherein $R_4$, $R_5$ and $R_3$ are as defined for formula I. Analogous with the compounds of formula I, depending on which of the above-mentioned five-membered azole rings the substituent $R_3$ denotes, the compounds of formula III' can be divided into six groups a to f, each of which groups represents a preferred embodiment. Particularly preferred compounds of formula III' are those which lead to the final products listed in Tables 1 to 5 and those which are explicitly indicated in Table 6.

The starting materials indicated in variants (a), (b) and (c) are known or can be prepared by methods analogous to those for the preparation of the known substances.

The preparatory process described, including all variants (a), (b), (c) and the etherification reactions, constitutes an object of the present invention.

The compounds of formula I may exist in different tautomeric forms, viz. in the keto or enol form or in a mixture of these forms. The present invention relates both to the individual tautomers and to their mixtures, as well as to the salts of each of these forms and to the preparation thereof.

The invention also relates to a method of protecting animals from attack by parasitic helminths, which comprises applying the compounds of formula I, or the formulations containing them, as additives to the solid or liquid feeds or also orally in solid or liquid form, by injection or by the pour-on method.

The compounds of formula I may be used in all tautomeric forms and mixtures thereof, or in the form of their salts, in each of the helminth control methods or anthelmintic compositions of this invention.

Among the endoparasites which occur in warm-blooded animals, the helminths cause severe damage. For example, animals attacked by these parasites are not only retarded in their growth, but in some cases suffer such harmful physiological effects that they die. It is therefore of great importance to develop agents which are suitable for controlling helminths and their development stages and to prevent attack by these parasites. Particularly dangerous helminth infestations are those caused in the gastrointestinal tract and other organs by parasitic nematodes, cestodes and trematodes, and especially in ruminants such as sheep, cattle and goats, as well as horses, pigs, deer, dogs, cats and poultry.

The damage caused by helminthiases can be substantial whenever herds of cattle fall victim to chronic and, in particular, epidemic attack. Such damage takes the form inter alia of diminution of useful performance, weakened resistance and increased mortality. The control and prevention of helminth infestation are therefore of the utmost importance to avoid or reduce such damage, especially damage having serious economic consequences.

Throughout this specification, the term "helminths" will be understood as meaning in particular parasitic worms which belong to the phyla Platyhelminthes (cestodes, trematodes) and Nemathelminthes (nematodes and related species), i.e. cestodes, trematodes and nematodes of the gastrointestinal tract and other organs (e.g. liver, lungs, kidneys, lymphatic vessels, blood etc.). Although a range of compounds having anthelminthic activity are known and have been proposed for controlling the different helminth species, they are not entirely satisfactory, either because it is not possible to exploit their activity spectrum fully when administered in well tolerated doses or because they exhibit undesirable side-effects or characteristics when administered in therapeutic doses. In this regard, the increasing resistance being encountered at the present time to specific classes of compound is an ever more significant factor. Although, for example, the prior art compound "albendazole" (British patent specification No. 1 464 326; *Am. J. Vet. Res.* 38, 1425–1426 (1977); *Am. J. Vet. Res.* 37, 1515–1516 (1976); *Am. J. Vet. Res.* 38, 807–808 (1977); *Am. J. Vet. Res.* 38, 1247–1248 (1977)) has a limited activity spectrum as anthelmintic when administered to ruminants, its activity e.g. against benzimidazole-resistant nematodes and adult liver flukes is completely inadequate. In particular, the pathologically important immature migratory forms of the last mentioned parasites are not attacked when the compound is administered in doses which are tolerated by the host animal.

Surprisingly, it has now been found that the compounds of formula I have both a potent anthelmintic activity with a broad activity spectrum against nematodes, cestodes and trematodes and, in addition, a low toxicity to warm-blooded animals.

The novel compounds of formula I of the invention are suitable e.g. for controlling parasitic nematodes of the orders (according to the classification of K. I. Skrajabin)
Rhabditida
Ascaridida
Spirurida
Trichocephalida
or for controlling cestodes of the orders (according to the classification of Wardle and McLeod)
Cyclophyllidae
Pseudophyllidae
or for controlling trematodes of the order
Digenea
in domestic animals and product livestock such as cattle, sheep, goats, horses, pigs, cats, dogs and poultry. The compounds of formula I can be administered to the animals in both individual and repeated doses. Depending on the species of animal, the individual doses are preferably administered in amounts ranging from 1 to 500 mg per kg of body weight. A better activity is sometimes achieved by protracted administration, or lower doses may suffice.

The compositions of this invention are prepared by bringing the compounds of formula I into contact with liquid and/or solid formulation adjuvants by stepwise mixing or grinding such that the formulation is able to exert its anthelmintic activity in optimum manner in accordance with the mode of application.

The formulation steps may be complemented by kneading, granulating and, if desired, pelleting.

Suitable formulation adjuvants are for example solid carriers, solvents and, optionally, surface-active compounds (surfactants).

The following formulation adjuvants are employed for preparing the compositions of the invention: solid carriers, e.g. kaolin, talc, bentonite, common salt, calcium phosphate, carbohydrates, cellulose powder, cottonseed meal, polyethylene glycol ether, optionally binders such as gelatin, soluble cellulose derivatives, if desired with the addition of surface-active compounds such as ionic or non-ionic dispersants; natural mineral fillers such as calcite, montmorillonite or attapulgite. To improve the physical properties it is also possible to add highly dispersed silicic acid or highly dispersed adsorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant material.

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil.

Frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-insoluble adducts of polyethylene oxide with polypropylene glycol, ethylenediaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual" MC Publishing Corp., Ridgewood, N.J., 1981; Helmut Stache, "Tensid-Taschenbuch" (Handbook of Surfactants), Carl Hanser Verlag, Munich/Vienna, 1981.

Suitable binders for tablets and boluses are chemically modified natural polymers which are soluble in water or alcohol, e.g. starch, cellulose or protein derivatives (e.g. methyl cellulose, carboxymethyl cellulose, ethyl hydroxyethyl cellulose, proteins such as zein, gelatin and the like), as well as synthetic polymers such as polyvinyl alcohol, polyvinyl pyrrolidone etc. Tablets also contain fillers (e.g. starch, microcrystalline cellulose, sugar, lactose etc.), glidants and disintegrators.

If the anthelmintic compositions are in the form of feed concentrates, then suitable carriers are for example production feeds, cereal feeds or protein concentrates. In addition to the active ingredients, such feeds can contain additives, vitamins, antibiotics, chemotherapeutical agents or other pesticides, in particular bacteriostats, fungistats, coccidiostats or also hormone preparations, substances having anabolic action or other substances which promote growth, enhance the quality of the flesh of slaughter animals, or which are otherwise beneficial to the organism. If the compositions or the compounds of formula I contained therein are added direct to the solid or liquid feed, then the ready prepared feed contains the active ingredient preferably in a concentration of about 0.0005 to 0.02 percent by weight (5–200 ppm).

The compositions of the invention are administered to the animals to be treated perorally, parenterally, subcutaneously or topically, and are in the form of solutions, emulsions, suspensions (drenches), powders, tablets, boluses and capsules.

The anthelmintic compositions of this invention usually contain 0.1 to 99% by weight, preferably 0.1 to 95% by weight, of a compound of formula I, 99.9 to 1% by weight, preferably 99.9 to 5% by weight, of a solid or liquid adjuvant, and 0 to 25% by weight, preferably 0.1 to 25% by weight, of a surfactant.

Whereas commercial products will be preferably formulated as concentrates, the end user will normally employ dilute formulations.

The compositions may also contain further ingredients such as stabilisers, antifoams, viscosity regulators, binders, tackifiers as well as fertilisers or other active ingredients in order to obtain special effects.

Such anthelmintic compositions employed by the end user likewise constitute an object of the present invention.

The invention is illustrated in more detailed by the following non-limitative Examples.

PREPARATORY EXAMPLE

Example 1

Preparation of

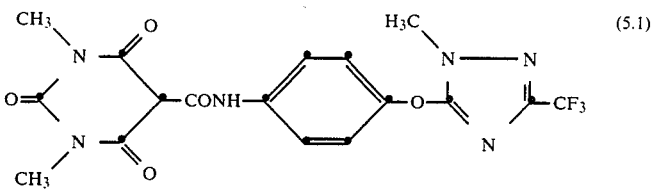

(5.1)

1,3-dimethyl-5-[4-(1-methyl-3-trifluoromethyl-1H-1,2,4-triazol-5-yloxy)phenylcarbamoyl]barbituric acid (a) Preparation of the starting material 1-methyl-3-trifluoromethyl-5-(4-aminophenoxy)-1H-1,2,4-triazole 8 g of pulverised KOH are added to 10.9 g of p-aminophenol in 120 ml of dimethyl sulfoxide, and the mixture is stirred for ½ hour. Then 22.9 g of 1-methyl-3-trifluoromethyl-5-methylsulfonyl-1H-1,2,4-triazole are added, the reaction mixture is stirred for a further 2 hours and subsequently poured into 1 liter of ice water. The precipitated product is isolated by filtration, washed with water and dried. Yield: 19.6 g (76% of theory). Melting point: 111°14 112° C.

(b) Preparation of the final product 22.8 g of 1,3-dimethyl-5-ethoxycarbonylbarbituric acid and 25.8 g of 1-methyl-3-trifluoromethyl-5-(4-aminophenoxy)-1H-1,2,4-triazole are heated under reflux in 200 ml of toluene for 4 hours. The crude product, which precipitates on cooling to room temperature, is isolated by filtration, washed with diethyl ether and dried. Yield: 39.2 g (89% of theory). Melting point: 202°-204° C.

Example 2

Preparation of

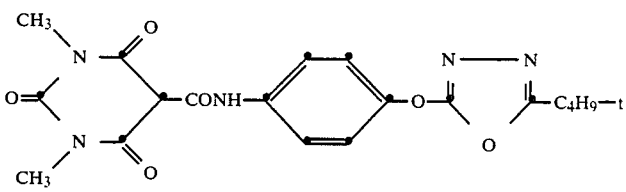

(4.1)

1,3-dimethyl-5-[4-(5-tert-butyl-1,3,4-oxadiazol-2-yloxy)phenylcarbamoyl]barbituric acid (a) Preparation of the starting material 5-tert-butyl-2-(4-aminophenoxy)-1,3,4-oxadiazole 7.3 g of pulverised KOH are added to 10.9 g of 4-aminophenol in 100 ml of dimethyl sulfoxide, and the mixture is stirred for 15 minutes. Then 20.4 g of 5-tert-butyl-2-methylsulfonyl-1,3,4-oxadiazole are added, the reaction mixture is stirred for 12 hours at room temperature and poured into ice water. The mixture is extracted with diethyl ether and the combined extracts are dried and concentrated by evaporation. Petroleum ether is added to the oily residue, whereupon the product crystallises. The product is then isolated by filtration and dried. Yield: 16.5 g (71% of theory). Melting point: 80°-81° C.

(b) Preparation of the final product 22.8 g of 1,3-dimethyl-5-ethoxycarbonylbarbituric acid and 23.3 g of 5-tert-butyl-2-(4-aminophenoxy)-1,3,4-oxadiazole are heated under reflux in 250 ml of toluene for 4 hours. The product, which precipitates on cooling, is isolated by filtration, washed with diethyl ether and dried. Yield: 37.7 g (91% of theory). Melting point: 200°-203° C.

(c)

The preparation of 5-tert-butyl-1,3,4-oxadiazole and of further 5-substituted 1,3,4-oxadiazoles is described in the literature (q.v. German Offenlegungsschrift No. 31 45 422 A1).

Example 3

Preparation of

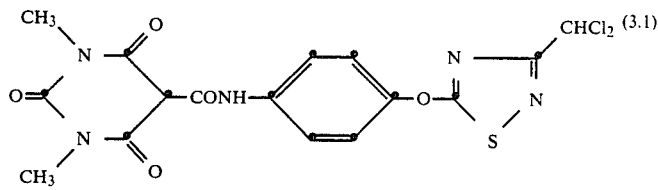

(3.1)

1,3-dimethyl-5-[4-(3-dichloromethyl-1,2,4-thiadiazol-5-yloxy)phenylcarbamoyl]barbituric acid (a) Preparation of the starting material 3-dichloromethyl-5-(4-aminophenoxy)-1,2,4-thiadiazole 5.5 g of 4-aminophenyl and 5.6 g of pulverised KOH are stirred in 150 ml of dimethyl sulfoxide for 30 minutes at room temperature. Then 10.0 g of 5-chloro-3-dichloromethyl-1,2,4-thiadiazole in 50 ml of dimethyl sulfoxide are added dropwise, whereupon the temperature rises to 40° C. After stirring for 2 hours, the reaction mixture is poured into ice water and the product is extracted with ethyl acetate. The combined extracts are dried and concentrated by evaporation. The oily crude product is purified with silica gel. Yield: 8.5 g of the title compound in the form of a yellow oil which is employed in the next step.
(b) Preparation of the final product A solution of 12 g of 1,3-dimethyl-5-ethoxycarbonylbarbituric acid and 15 g of 3-dichloromethyl-5-(4-aminphenoxy)-1,2,4-thiadiazole in 300 ml of toluene is heated under reflux for 2 hours. The yellow reaction solution is subsequently evaporated to dryness and the residue is stirred in dichloromethane, whereupon the title compound crystallises. This compound is then isolated by filtration and dried. Yield: 19 g of pale yellow crystals.
Melting point: 195°–198° C.

Example 4

Preparation of

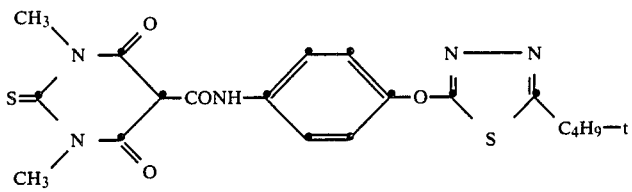

1,3-dimethyl-5-[4-(5-tert-butyl-1,3,4-thiadiazol-2-yloxy)phenylcarbamoyl]-2-thiobarbituric acid 1.7 g of 1,3-dimethyl-5-ethoxycarbonylbarbituric acid and 1.75 g of 4-(5-tert-butyl-1,3,4-thiadiazol-2-yloxy)aniline are heated under reflux in 30 ml of toluene for 30 hours. After cooling to room temperature, the mixture is diluted with 40 ml of hexane, the resultant precipitate is isolated by filtration, washed with isopropanol and dried. Yield: 2.5 g (82% of theory).
Melting point: 174°–176° C.

Example 5

Preparation of

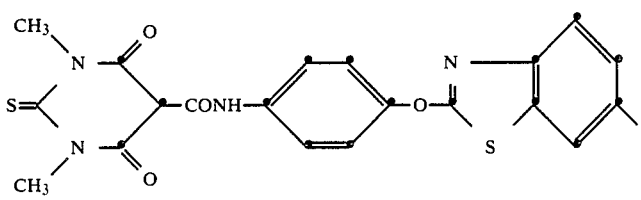

1,3-dimethyl-5-[4-(6-chlorobenzothiazol-2-yloxy)phenylcarbamoyl]-2-thiobarbituric acid 2.5 g of 1,3-dimethyl-5-ethoxycarbonylthiobarbituric acid and 2.8 g of 4-(5-chlorobenzothiazol-2-yloxy)aniline are mixed with 30 ml of ehtnaol and 3 ml of dimethylformamide, and the mixture is heated under reflux for 7 hours. On cooling to room temperature a precipitate forms which is isolated by filtration, washed with ehtanol and dried. Yield: 3.7 g (75% of theory). Melting point: 213°–215° C.

Example 6

Preparation of

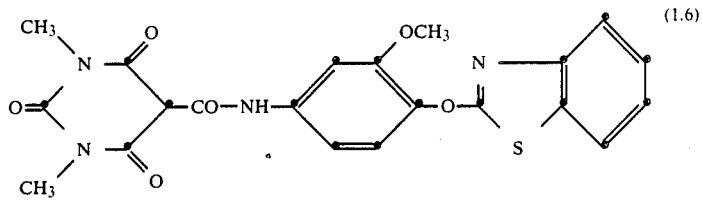

1,3-dimethyl-5-[3-methoxy-4-(benzothiazol-2-yloxy)phenylcarbonyl]barbituric acid (a) Preparation of the starting material 1,3-dimethyl-5-(4-hydroxy-3-methoxyphenylcarbamoyl)barbituric acid 6.85 g of 1,3-dimethyl-5-ethoxycarbonylbarbituric acid and 4.2 g of 4-hydroxy-3-methoxyaniline are suspended in 60 ml of toluene, and the suspension is heated under reflux for 3 hours, whereupon ethanol escapes. On cooling to room temperature a precipitate forms which is isolated by filtration, washed with ethanol and dried. Yield: 8.3 g (86% of theory). Melting point: 252°–253° C.
(b) Preparation of the final product 1.3 g of 85% KOH are added to 3.2 g of 1,3-dimethyl-5-(4-hydroxy-3-methoxyphenylcarbamoyl)barbituric acid in 25 ml of toluene and 15 ml of dimethyl sulfoxide. The mixture is dewatered with a water separator at reflux temperature. The toluene is distilled off and then 1.7 g of 2-chlorobenzothiazole are added and the bath temperature is slowly increased to a temperature in the range from 40° to 60° C. The mixture is kept at this temperature for a further 10 hours, then cooled to room temperature and neutralised with dilute, aqueous HCl. The resultant precipitate is isolated by filtration, washed with water and ethanol and dried.
Melting point: 210°–211° C.

Example 7

Preparation of

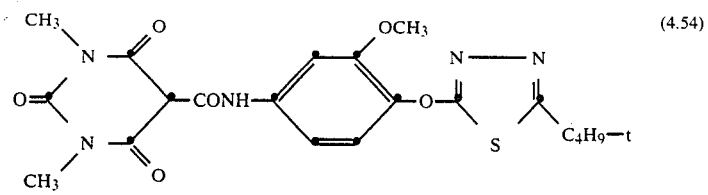

(4.54)

1,3-dimethyl-5-[3-methoxy-4-(5-tert-butyl-1,3,4-thiadiazol-2-yloxy)phenylcarbamoyl]barbituric acid 1.7 g of 1,3-dimethyl-2-barbituric acid and 2.7 g of 3-methoxy-4-(5-tert-butyl-1,3,4-thiadiazol-2-yloxy)-phenylisocyanate are suspended in 10 ml of xylene, and 0.2 g of triethylamine is added dropwise to the suspension, whereupon the temperature rises to 45° to 50° C. After the addition of a further 10 ml of xylene, the mixture is stirred at this temperature for 18 hours. Then about ⅓ of the xylene is distilled off and, after cooling to room temperature, the reaction mixture is diluted with 50 ml of hexane, whereupon a crystalline precipitate forms. This precipitate is isolated by filtration, washed with water and then with isopropanol and dried. Yield: 3.6 g (82% of theory). Melting point: 178°–179° C.

The following compounds of formula I and intermediates of formula III' can be obtained by procedures analogous to those described above.

TABLE 1

Compounds of formula I, wherein

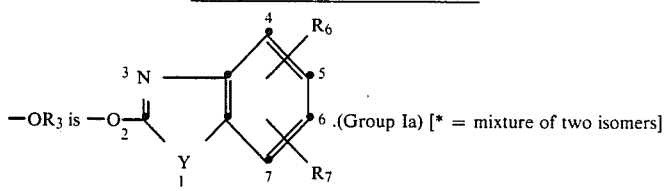

$-OR_3$ is $-O-\overset{Y}{\underset{\parallel}{C}}-$ (Group Ia) [* = mixture of two isomers]

| Comp. | X | $R_1$ | $R_2$ | $R_4$ | $R_5$ | Position of $-OR_3$ | Y | $R_6$ | $R_7$ | m.p. [°C.] |
|---|---|---|---|---|---|---|---|---|---|---|
| 1.1 | S | $CH_3$ | $CH_3$ | H | H | 4 | S | 6-Cl | H | 213–215 |
| 1.2 | O | $CH_3$ | $OCH_3$ | H | H | 4 | S | 6-Cl | H | 199–203 |
| 1.3 | S | $CH_3$ | $CH_3$ | 3-$CH_3$ | H | 4 | S | 6-F | H | |
| 1.4 | S | $CH_3$ | $CH_3$ | H | H | 4 | S | H | H | 217–219 |
| 1.5 | O | $CH_3$ | $CH_3$ | H | H | 4 | S | 6-Cl | H | 234–235 |
| 1.6 | O | $CH_3$ | $CH_3$ | 3-$OCH_3$ | H | 4 | S | H | H | 210–211 |
| 1.7 | O | $CH_3$ | $CH_3$ | 3-$CH_3$ | H | 4 | S | 6-Cl | H | |
| 1.8 | O | $CH_3$ | $CH_3$ | H | H | 4 | S | 6-Br | H | 237–240 |
| 1.9 | O | $CH_3$ | $CH_3$ | H | H | 4 | S | 5,(7)-Cl* | 6-Cl | 193–203 |
| 1.10 | O | $CH_3$ | $C_2H_5$ | H | H | 4 | S | 6-F | H | |
| 1.11 | O | $CH_3$ | $CH_3$ | 3-$OCH_3$ | H | 4 | S | 6-Cl | H | 210–214 |
| 1.12 | S | $CH_3$ | $CH_3$ | H | H | 4 | $NCH_3$ | 6-Cl | H | |
| 1.13 | O | $CH_3$ | $CH_3$ | H | H | 4 | $NCH_3$ | 6-Cl | H | |
| 1.14 | O | $CH_3$ | $C_2H_5$ | H | H | 3 | S | 6-Cl | H | |
| 1.15 | S | $CH_3$ | $CH_3$ | H | H | 3 | S | 6-Cl | H | |
| 1.16 | O | $CH_3$ | $CH_3$ | H | H | 4 | O | H | H | 211–215 |
| 1.17 | O | $CH_3$ | $CH_3$ | H | H | 3 | O | 6-Cl | H | |
| 1.18 | O | $CH_3$ | $CH_3$ | H | H | 4 | O | 6-Cl | H | |
| 1.19 | O | $CH_3$ | $OCH_3$ | H | H | 4 | O | 6-Cl | H | |
| 1.20 | S | $CH_3$ | $CH_3$ | H | H | 4 | O | H | H | |
| 1.21 | O | $CH_3$ | $OCH_3$ | 3-$CH_3$ | H | 4 | O | 6-Cl | H | |
| 1.22 | O | $CH_3$ | $CH_3$ | H | H | 4 | NH | 6-Cl | H | |
| 1.23 | O | $CH_3$ | $OCH_3$ | H | H | 4 | NH | 6-Cl | H | |
| 1.24 | O | $CH_3$ | $CH_3$ | 3-$CH_3$ | H | 4 | NH | 6-Cl | H | |
| 1.25 | S | $CH_3$ | $CH_3$ | H | H | 4 | NH | 6-Cl | H | |
| 1.26 | S | $CH_3$ | $OCH_3$ | H | H | 4 | NH | 6-Cl | H | |
| 1.27 | O | $CH_3$ | $CH_3$ | H | H | 4 | NH | H | H | 262–265 |
| 1.28 | O | $CH_3$ | $CH_3$ | H | H | 3 | NH | H | H | 240–242 |
| 1.29 | O | $CH_3$ | $OCH_3$ | H | H | 2 | NH | 6-Br | H | |
| 1.30 | O | allyl | $CH_3$ | H | H | 4 | O | 6-Cl | H | |
| 1.31 | O | cyclopropyl | $CH_3$ | H | H | 4 | O | 6-Cl | H | |
| 1.32 | O | $CH_3$ | $CH_3$ | H | H | 4 | S | H | H | 207–208 |
| 1.33 | S | $CH_3$ | $CH_3$ | 3-$OCH_3$ | H | 4 | S | H | H | |
| 1.34 | O | $CH_3$ | $CH_3$ | H | H | 4 | $NCH_3$ | H | H | |
| 1.35 | O | $CH_3$ | $CH_3$ | H | H | 4 | $NCH_3$ | 6-$NO_2$ | H | 227–230 |
| 1.36 | O | $CH_3$ | $CH_3$ | H | H | 4 | $NCH_3$ | 5-$NO_2$ | H | |
| 1.37 | O | $CH_3$ | $CH_3$ | H | H | 3 | S | H | H | 183–184 |
| 1.38 | O | $CH_3$ | $CH_3$ | H | H | 4 | S | 6-F | H | 181–183 |
| 1.39 | O | $CH_3$ | $CH_3$ | H | H | 4 | S | 6-$CF_3$ | H | 186–190 |
| 1.40 | O | $CH_3$ | $CH_3$ | H | H | 4 | S | 6-$OCH_3$ | H | 204–205 |
| 1.41 | O | $CH_3$ | $CH_3$ | H | H | 4 | S | 6-$OCF_3$ | H | 181–183 |
| 1.42 | O | $CH_3$ | $OCH_3$ | H | H | 4 | S | 6-$OCF_3$ | H | |
| 1.43 | O | $CH_3$ | $CH_3$ | H | H | 4 | S | 6-F | 5,(7)-Cl* | 190–194 |

TABLE 1-continued

Compounds of formula I, wherein

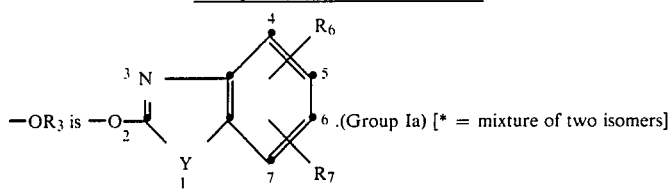

$-OR_3$ is $-O-\overset{\overset{3}{N}}{\underset{2}{C}}$ (phenyl ring with positions 4, 5, 6, 7 and $R_6$, $R_7$, Y) (Group Ia) [* = mixture of two isomers]

| Comp. | X | $R_1$ | $R_2$ | $R_4$ | $R_5$ | Position of $-OR_3$ | Y | $R_6$ | $R_7$ | m.p. [°C.] |
|---|---|---|---|---|---|---|---|---|---|---|
| 1.44 | O | $CH_3$ | $CH_3$ | H | H | 4 | S | 6-Cl | 4-$CH_3$ | |
| 1.45 | O | $CH_3$ | $CH_3$ | H | H | 4 | S | 6-F | 5-F | |
| 1.46 | O | $CH_3$ | $OCH_3$ | H | H | 4 | S | 6-F | 5-F | |
| 1.47 | S | $CH_3$ | $CH_3$ | H | H | 4 | S | 5-Cl | H | |
| 1.48 | O | $CH_3$ | $CH_3$ | H | H | 4 | S | 6-Cl | 5-Cl | |
| 1.49 | O | $CH_3$ | $CH_3$ | H | H | 4 | S | 6-Cl | 7-Cl | |
| 1.50 | S | $CH_3$ | $CH_3$ | 3-$OCH_3$ | H | 4 | S | 6-Cl | 5-$CH_3$ | |
| 1.51 | O | $CH_3$ | $CH_3$ | H | H | 3 | S | 6-Cl | 5-$CH_3$ | |
| 1.52 | O | $CH_3$ | $CH_3$ | 3-$OCH_3$ | H | 4 | S | 6-F | 5-Cl | |
| 1.53 | O | $CH_3$ | $CH_3$ | H | H | 4 | S | 6-F | 5-Cl | 216–217 |
| 1.54 | O | $CH_3$ | $CH_3$ | H | H | 4 | S | 6-F | 7-Cl | 205–208 |
| 1.55 | O | $CH_3$ | $OCH_3$ | H | H | 4 | S | 6-F | 5-Cl | 192–194 |
| 1.56 | O | $CH_3$ | $OCH_3$ | H | H | 4 | S | 6-F | 7-Cl | 215–218 |
| 1.57 | S | $CH_3$ | $CH_3$ | H | H | 4 | S | 6-F | 5-Cl | 220–221 |
| 1.58 | S | $CH_3$ | $CH_3$ | H | H | 4 | S | 6-F | 7-Cl | 225–226 |
| 1.59 | O | $CH_3$ | $CH_3$ | H | H | 4 | S | 5-Cl | H | |
| 1.60 | O | $CH_3$ | $CH_3$ | 4-$OCH_3$ | H | 3 | S | 6-Cl | H | 189–192 |
| 1.61 | S | $CH_3$ | $CH_3$ | 3-$OCH_3$ | H | 4 | S | 6-Cl | H | |
| 1.62 | O | $CH_3$ | $CH_3$ | 3-$OCH_3$ | H | 4 | S | 6-$OCF_3$ | H | |
| 1.63 | S | $CH_3$ | $CH_3$ | H | H | 4 | S | 6-$OCF_3$ | H | 227–229 |
| 1.64 | O | $C_2H_5$ | $CH_3$ | H | H | 4 | S | 6-Cl | H | 152–155 |
| 1.65 | O | $CH_2CH=CH_2$ | $CH_3$ | H | H | 4 | S | 6-Cl | H | 121 Decomp. |
| 1.66 | O | $CH_3$ | $CH_3$ | H | H | 4 | S | 6-$NO_2$ | H | |
| 1.67 | S | $CH_3$ | $CH_3$ | H | H | 4 | S | 6-$OC_2H_5$ | H | |
| 1.68 | O | $CH_3$ | $CH_3$ | H | H | 4 | S | 4-F | 7-F | |
| 1.69 | O | $CH_3$ | $CH_3$ | H | H | 4 | O | 6-Cl | H | |
| 1.70 | O | $CH_3$ | $CH_3$ | H | 3-$OCH_3$ | 4 | O | H | 5-Cl | |
| 1.71 | O | $CH_3$ | $CH_3$ | H | H | 4 | O | H | 5-$CH_3$ | |
| 1.72 | O | $CH_3$ | $CH_3$ | H | H | 4 | O | 6-$NO_2$ | 5-$CH_3$ | |
| 1.73 | S | $CH_3$ | $CH_3$ | H | H | 4 | O | 6-Cl | H | |
| 1.74 | S | $CH_3$ | $CH_3$ | H | H | 4 | O | H | 5-Cl | |
| 1.75 | S | $CH_3$ | $CH_3$ | H | 4-$OCH_3$ | 3 | O | H | 5-$CH_3$ | |
| 1.76 | O | $CH_3$ | $CH_3$ | H | 3-$OCH_3$ | 4 | S | 6-F | 5-Cl | |
| 1.77 | S | $CH_3$ | $CH_3$ | H | H | 4 | S | 6-F | H | 199–201 |
| 1.78 | S | $CH_3$ | $CH_3$ | H | H | 4 | S | 6-Cl | 7-F | 199–202 |
| 1.79 | O | $CH_3$ | $OCH_3$ | H | H | 4 | S | 6-Cl | 7-F | 195–201 |
| 1.80 | O | $CH_3$ | $CH_3$ | H | 3-$OCH_3$ | 4 | S | 6-Cl | 7-F | 188–194 |
| 1.81 | O | $CH_3$ | $CH_3$ | 2-$CH(CH_3)_2$ | H | 4 | S | 6-Cl | H | |
| 1.82 | S | $CH_3$ | $CH_3$ | 2-$CH(CH_3)_2$ | H | 4 | S | 6-Cl | H | |
| 1.83 | O | $CH_3$ | $CH_3$ | 2-$CH_3$ | 3-$CH_3$ | 4 | S | 6-Cl | H | |
| 1.84 | O | $CH_3$ | $CH_3$ | 2-$C_4H_9$—t | H | 4 | S | 6-Cl | H | |
| 1.85 | S | $CH_3$ | $CH_3$ | 2-$CH(CH_3)_2$ | H | 4 | S | 6-F | H | |
| 1.86 | S | $CH_3$ | $CH_3$ | 2-$CH(CH_3)_2$ | H | 4 | S | 6-F | 5-Cl | |
| 1.87 | O | $CH_3$ | $CH_3$ | 2-$C_3H_7$—n | H | 4 | S | 6-F | H | |
| 1.88 | O | $CH_3$ | $CH_3$ | 4-$CH_3$ | H | 3 | S | 6-Cl | H | |
| 1.89 | O | $CH_3$ | $CH_3$ | 4-$CH(CH_3)_2$ | H | 3 | S | 6-Cl | H | |
| 1.90 | S | $CH_3$ | $CH_3$ | 4-$C_2H_5$ | H | 3 | S | 6-Cl | H | |
| 1.91 | O | $CH_3$ | $CH_3$ | 3-$OCH_3$ | H | 4 | S | 6-F | 5,(7)-Cl* | 210–215 |

TABLE 2

Compounds of formula I, wherein (Group Ib)

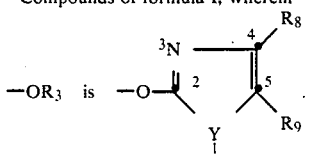

| Comp. | X | $R_1$ | $R_2$ | $R_4$ | $R_5$ | Position of $-OR_3$ | Y | $R_8$ | $R_9$ | m.p. [°C.] |
|---|---|---|---|---|---|---|---|---|---|---|
| 2.1 | O | $CH_3$ | $CH_3$ | H | H | 4 | NH | H | H | |
| 2.2 | O | $CH_3$ | $CH_3$ | H | H | 4 | $NCH_3$ | Cl | Cl | 220–222 |
| 2.3 | O | $CH_3$ | $CH_3$ | H | H | 4 | NH | $OCH_3$ | H | |
| 2.4 | S | $CH_3$ | $CH_3$ | H | H | 4 | NH | $SCH_3$ | H | |
| 2.5 | S | $CH_3$ | $CH_3$ | H | H | 4 | NH | $CH_3$ | H | |

TABLE 2-continued

Compounds of formula I, wherein $-OR_3$ is 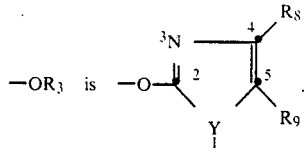 (Group Ib)

| Comp. | X | $R_1$ | $R_2$ | $R_4$ | $R_5$ | Position of $-OR_3$ | Y | $R_8$ | $R_9$ | m.p. [°C.] |
|---|---|---|---|---|---|---|---|---|---|---|
| 2.6 | O | $CH_3$ | $CH_3$ | H | H | 3 | NH | H | H | |
| 2.7 | O | $CH_3$ | $CH_3$ | H | H | 4 | O | H | H | |
| 2.8 | O | $CH_3$ | $CH_3$ | H | H | 4 | S | H | H | 148–150 |
| 2.9 | O | $CH_3$ | $OCH_3$ | H | H | 4 | O | $CH_3$ | H | |
| 2.10 | O | $CH_3$ | $CH_3$ | H | H | 4 | S | $CF_3$ | H | 180 |
| 2.11 | S | $CH_3$ | $CH_3$ | 2-$CH_3$ | 6-$CH_3$ | 4 | S | $CH_3$ | H | |
| 2.12 | S | $CH_3$ | $CH_3$ | H | H | 4 | S | H | H | |
| 2.13 | O | $CH_3$ | $CH_3$ | H | H | 2 | NH | H | H | |
| 2.14 | O | $CH_3$ | $CH_3$ | H | H | 4 | S | H | $NO_2$ | |
| 2.15 | O | $CH_3$ | $OCH_3$ | H | H | 4 | S | H | $NO_2$ | |
| 2.16 | O | $CH_3$ | $OCH_3$ | H | H | 4 | S | $CF_3$ | H | |
| 2.17 | O | $CH_3$ | $CH_3$ | 3-$OCH_3$ | H | 4 | S | $CF_3$ | H | |
| 2.18 | S | $CH_3$ | $CH_3$ | H | H | 4 | S | $CF_3$ | H | |
| 2.19 | S | $CH_3$ | $CH_3$ | 4-$OCH_3$ | H | 3 | S | $CF_3$ | H | |

TABLE 3

Compounds of formula I, wherein $R_2$ is $CH_3$ and $-OR_3$ is 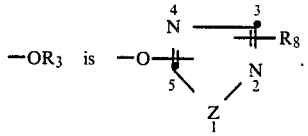 (Group Ic)

| Comp. | X | $R_1$ | $R_4$ | $R_5$ | Position of $-OR_3$ | Position of O in $R_3$ | $R_8$ | Position of $R_8$ | Z | m.p. [°C.] |
|---|---|---|---|---|---|---|---|---|---|---|
| 3.1 | O | $CH_3$ | H | H | 4 | 5 | $CHCl_2$ | 3 | S | 195–198 |
| 3.2 | O | $CH_3$ | H | H | 4 | 5 | $CH_3$ | 3 | S | |
| 3.3 | O | $CH_3$ | H | H | 4 | 5 | $CH_3$ | 3 | O | |
| 3.4 | O | $CH_3$ | H | H | 4 | 5 | $CHCl_2$ | 3 | O | |
| 3.5 | O | $CH_3$ | H | H | 4 | 5 | $CF_3$ | 3 | O | |
| 3.6 | S | $CH_3$ | H | H | 4 | 5 | $CH_3$ | 3 | S | |
| 3.7 | S | $CH_3$ | H | H | 4 | 5 | $CHCl_2$ | 3 | O | |
| 3.8 | O | $OCH_3$ | H | H | 4 | 5 | $CH_3$ | 3 | O | |
| 3.9 | O | $OCH_3$ | 3-$CH_3$ | H | 4 | 5 | H | 3 | O | |
| 3.10 | S | $OCH_3$ | H | H | 4 | 5 | $CCl_3$ | 3 | S | |
| 3.11 | O | $CH_3$ | H | H | 4 | 5 | $CH_3$ | 3 | NH | |
| 3.12 | S | $CH_3$ | H | H | 4 | 5 | $CH_2Cl$ | 3 | NH | |
| 3.13 | O | $CH_3$ | 3-$CH_3$ | H | 4 | 5 | $CF_3$ | 3 | NH | |
| 3.14 | O | $CH_3$ | H | H | 4 | 3 | H | 5 | S | |
| 3.15 | O | $CH_3$ | H | H | 4 | 3 | $CH_3$ | 5 | O | |
| 3.16 | S | $CH_3$ | H | H | 4 | 3 | $CH_2Cl$ | 5 | NH | |
| 3.17 | O | $CH_3$ | 6-$CH_3$ | H | 3 | 5 | $CF_3$ | 3 | S | 179–180 |
| 3.18 | O | $CH_3$ | 2-$CH_3$ | H | 4 | 5 | $CF_3$ | 3 | S | 180–181 |
| 3.19 | O | $CH_3$ | H | H | 4 | 5 | $CF_3$ | 3 | S | 170–171 |
| 3.20 | O | $CH_3$ | H | H | 4 | 5 | Cl | 3 | S | 185–187 |
| 3.21 | S | $CH_3$ | H | H | 4 | 5 | $CHCl_2$ | 3 | S | |

TABLE 4

Compounds of formula I, wherein $R_2$ is $CH_3$ and $-OR_3$ is 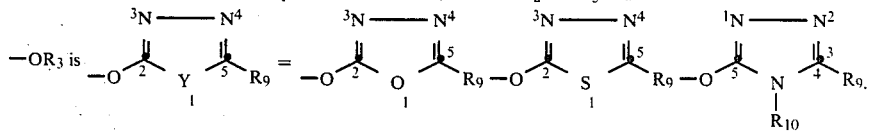 (Group Ie)

| Comp. | X | $R_1$ | $R_4$ | $R_5$ | Position of $-OR_3$ | Y | $R_9$ | $R_{10}$ | m.p. [°C.] |
|---|---|---|---|---|---|---|---|---|---|
| 4.1 | O | $CH_3$ | H | H | 4 | O | $C_4H_9$—t | | 200–203 |
| 4.2 | O | $CH_3$ | H | H | 4 | S | $C_4H_9$—t | | 176–177 |
| 4.3 | S | $CH_3$ | H | H | 4 | S | $C_4H_9$—t | | 174–176 |
| 4.4 | O | $CH_3$ | H | H | 4 | S | H | | |
| 4.5 | O | $CH_3$ | H | H | 4 | S | $CF_3$ | | |
| 4.6 | O | $CH_3$ | H | H | 4 | O | $CF_3$ | | |

TABLE 4-continued

| | | | | | | | | |
|---|---|---|---|---|---|---|---|---|
| 4.7 | O | CH₃ | 3-CH₃ | H | 4 | O | C₄H₉—t | |
| 4.8 | O | CH₃ | 2-CH₃ | 6-CH₃ | 4 | O | C₄H₉—t | 203-204 |
| 4.9 | O | CH₃ | 2-CH(CH₃)₂ | H | 4 | O | C₄H₉—t | |
| 4.10 | O | CH₃ | H | H | 4 | O | CH(CH₃)₂ | 168-172 |
| 4.11 | O | CH₃ | 2-CH₃ | 6-CH₃ | 4 | O | CH(CH₃)₂ | |
| 4.12 | O | CH₃ | H | H | 4 | O | CH₃ | |
| 4.13 | O | OCH₃ | H | H | 4 | O | CH₃ | |
| 4.14 | O | CH₃ | 2-CH₃ | 6-CH₃ | 4 | O | CH₃ | |
| 4.15 | O | CH₃ | 2-CH(CH₃)₂ | H | 4 | O | CH₃ | |
| 4.16 | O | CH₃ | H | H | 4 | O | CCl₃ | |
| 4.17 | O | CH₃ | H | H | 4 | S | C₄H₉—s | |
| 4.18 | O | CH₃ | H | H | 4 | O | CF₃ | |
| 4.19 | O | CH₃ | 2-CH₃ | 6-CH₃ | 4 | O | CF₃ | |
| 4.20 | O | CH₃ | 2-CF₃ | H | 4 | S | C₄H₉—t | 210-211 |
| 4.21 | O | CH₃ | 2-CH₃ | 6-CH₃ | 4 | O | C₄H₉—i | |
| 4.22 | O | CH₃ | H | H | 4 | S | C₄H₉—s | |
| 4.23 | O | CH₃ | 2-CH₃ | 6-CH₃ | 4 | O | CH(C₂H₅)₂ | |
| 4.24 | O | CH₃ | H | H | 4 | S | CF₃ | |
| 4.25 | O | CH₃ | H | H | 4 | S | C(CH₃)₃ | |
| 4.26 | O | CH₃ | H | H | 4 | S | CH₃ | |
| 4.27 | S | CH₃ | H | H | 4 | O | CH(CH₃)₂ | |
| 4.28 | O | CH₃ | 2-CH₃ | 6-CH₃ | 4 | S | CF₃ | |
| 4.29 | O | CH₃ | 2-CH₃ | 6-CH₃ | 4 | S | CCl₃ | |
| 4.30 | O | CH₃ | H | H | 4 | NH | C₄H₉—t | |
| 4.31 | O | OCH₃ | H | H | 4 | NH | C₄H₉—i | |
| 4.32 | O | CH₃ | 2-CH₃ | 6-CH₃ | 4 | NH | CH(CH₃)₂ | |
| 4.33 | O | CH₃ | H | H | 4 | NH | CF₃ | |
| 4.34 | O | CH₃ | H | H | 4 | NH | CCl₃ | |
| 4.35 | O | CH₃ | H | H | 4 | NH | C₄H₉—n | |
| 4.36 | O | OCH₃ | H | H | 4 | NH | CF₃ | |
| 4.37 | S | CH₃ | H | H | 4 | O | C₄H₉—t | |
| 4.38 | S | CH₃ | 2-CH₃ | 6-CH₃ | 4 | O | CH₃ | |
| 4.39 | S | OCH₃ | H | H | 4 | O | CF₃ | |
| 4.40 | S | CH₃ | H | H | 4 | O | CF₃ | |
| 4.41 | S | CH₃ | 2-CH₃ | H | 4 | S | C₄H₉—t | |
| 4.42 | S | OCH₃ | H | H | 4 | O | C₄H₉—t | |
| 4.43 | S | CH₃ | 2-CH₃ | 6-CH₃ | 4 | S | CH₃ | |
| 4.44 | O | CH₃ | H | H | 3 | O | C₄H₉—t | 197-198 |
| 4.45 | O | CH₃ | H | H | 3 | S | C₄H₉—t | 148-149 |
| 4.46 | S | CH₃ | H | H | 3 | S | C₄H₉—t | |
| 4.47 | O | CH₃ | H | H | 3 | O | CH₃ | |
| 4.48 | O | CH₃ | H | H | 2 | O | CH₃ | |
| 4.49 | O | CH₃ | H | H | 2 | O | C₄H₉—t | |
| 4.50 | S | CH₃ | H | H | 2 | S | C₄H₉—t | |
| 4.51 | O | CH₃ | 2-CH₃ | H | 4 | S | C₄H₉—t | 172-173 |
| 4.52 | O | CH₃ | H | H | 4 | S | CH(CH₃)₂ | 150-151 |
| 4.53 | O | CH₃ | H | H | 3 | S | C₄H₉—i | 106-107 |
| 4.54 | O | CH₃ | 3-OCH₃ | H | 4 | S | C₄H₉—t | 178-179 |
| 4.55 | O | OCH₃ | H | H | 4 | S | C₄H₉—t | 132-133 |
| 4.56 | O | CH₃ | H | H | 4 | O | cyclopropyl | 192-195 |
| 4.57 | O | CH₃ | H | H | 3 | O | cyclopropyl | 148-151 |
| 4.58 | O | CH₃ | H | H | 4 | S | SCH(CH₃)₂ | 137 |
| 4.59 | O | CH₃ | 2-CH(CH₃)₂ | H | 4 | O | cyclopropyl | 150-152 |
| 4.60 | O | CH₃ | H | H | 4 | O | C₆H₅Cl(3) | 238-240 |
| 4.61 | O | CH₃ | H | H | 3 | O | C₆H₅Cl(3) | 220-225 |
| 4.62 | O | CH₃ | H | H | 4 | O | CH(CH₃)₂ | 168-172 |
| 4.63 | O | CH₃ | H | H | 3 | O | CH(CH₃)₂ | 165-167 |
| 4.64 | O | CH₃ | H | H | 4 | O | cyclohexyl | 190-192 |
| 4.65 | O | CH₃ | H | H | 3 | O | cyclohexyl | 171-173 |
| 4.66 | O | CH₃ | H | H | 4 | S | cyclohexyl | 173 |
| 4.67 | O | CH₃ | H | H | 4 | S | C₄H₉—t | 191-194** |
| 4.68 | O | CH₃ | 2-CH₃ | 6-CH₃ | 4 | O | cyclopropyl | |
| 4.69 | O | CH₃ | H | H | 4 | S | cyclopropyl | 148-149 |
| 4.70 | S | CH₃ | 4-OCH₃ | H | 3 | S | C₄H₉—t | |
| 4.71 | S | CH₃ | 3-OCH₃ | H | 4 | S | C₄H₉—t | 185-186 |
| 4.72 | O | CH₃ | 4-OCH₃ | H | 3 | S | cyclohexyl | |
| 4.73 | O | CH₃ | H | H | 4 | S | cyclohexyl | |
| 4.74 | O | C₂H₅ | H | H | 4 | S | cyclohexyl | |
| 4.75 | O | allyl | H | H | 4 | S | cyclohexyl | |
| 4.76 | S | CH₃ | H | H | 4 | S | cyclohexyl | |
| 4.77 | S | CH₃ | H | 4-OCH₃ | 3 | S | cyclohexyl | |
| 4.78 | O | CH₃ | 2-CH₃ | H | 4 | S | cyclohexyl | 165-166 |
| 4.79 | O | CH₃ | H | H | 4 | S |  | |

TABLE 4-continued

| Comp. | X | $R_1$ | $R_4$ | $R_5$ | Position of $-OR_3$ | | |  |
|---|---|---|---|---|---|---|---|---|
| 4.80 | S | $CH_3$ | H | H | 4 | S | 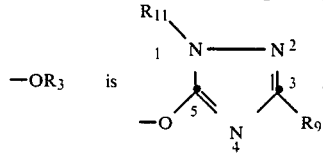 | |
| 4.81 | S | $CH_3$ | H | H | 4 | O | cyclopropyl | 193–194 |
| 4.82 | S | $CH_3$ | H | H | 3 | O | cyclopropyl | |
| 4.83 | S | $CH_3$ | 2-$CH(-CH_3)_2$ | H | 4 | O | cyclopropyl | 128–129 |
| 4.84 | S | $CH_3$ | H | H | 4 | O | $CH(CH_3)_2$ | |
| 4.85 | S | $CH_3$ | H | H | 3 | O | $CH(CH_3)_2$ | 164–167 |
| 4.86 | S | $CH_3$ | H | H | 4 | O | cyclohexyl | 180–184 |
| 4.87 | S | allyl | H | H | 4 | O | cyclopropyl | |
| 4.88 | O | $CH_3$ | 2-$C_4H_9$—t | H | 4 | O | $C_4H_9$—t | |
| 4.89 | S | $CH_3$ | 2-$C_4H_9$—t | H | 4 | S | $C_4H_9$—t | |
| 4.90 | O | $CH_3$ | 2-$C_4H_9$—t | H | 4 | S | cyclopropyl | |
| 4.91 | S | $CH_3$ | 2-$C_4H_9$—t | H | 4 | O | cyclopropyl | |
| 4.92 | O | $CH_3$ | 4-$C_2H_5$— | H | 3 | O | $C_4H_9$—t | |
| 4.93 | S | $CH_3$ | 4-$C_2H_5$ | H | 3 | O | $C_4H_9$—t | |
| 4.94 | O | $CH_3$ | 4-$C_2H_5$ | H | 3 | S | cyclopropyl | | where $Y = -N-$
                $|$
                $R_{10}$

| Comp. | X | $R_1$ | $R_4$ | $R_5$ | Position of $-OR_3$ | Y | $R_9$ | $R_{10}$ | m.p. [°C] |
|---|---|---|---|---|---|---|---|---|---|
| 4.95 | O | $CH_3$ | H | H | 4 | | $C_4H_9$—t | $CH_3$ | |
| 4.96 | O | $CH_3$ | H | H | 4 | | $C_4H_9$—t | $CH_3$ | |
| 4.97 | O | $CH_3$ | 2-$CH_3$ | 6-$CH_3$ | 4 | | $CF_3$ | $CH_3$ | |
| 4.98 | O | $CH_3$ | H | H | 4 | | $CH_3$ | $CH_3$ | |
| 4.99 | O | $CH_3$ | 2-$CH_3$ | 6-$CH_3$ | 4 | | $CF_3$ | $CH(CH_3)_2$ | |
| 4.100 | O | $CH_3$ | H | H | 4 | | $C_2F_5$ | $CH(CH_3)_2$ | |
| 4.101 | O | $CH_3$ | 2-$CH_3$ | 6-$CH_3$ | 4 | | $C_2F_5$ | $CH(CH_3)_2$ | |
| 4.102 | O | $OCH_3$ | H | H | 4 | | $CF_3$ | $CH_3$ | |
| 4.103 | O | $CH_3$ | 2-$CH_3$ | 6-$CH_3$ | 4 | | $C_2F_5$ | $CH_3$ | |
| 4.104 | O | $CH_3$ | 2-$CH(CH_3)_2$ | H | 4 | | $CF_3$ | $CH_3$ | |
| 4.105 | O | $CH_3$ | 2-$CH(CH_3)_2$ | H | 4 | | $CF_3$ | $CH(CH_3)_2$ | |
| 4.106 | S | $CH_3$ | H | H | 4 | | $C_4H_9$—t | $CH_3$ | |
| 4.107 | S | $CH_3$ | H | H | 4 | | $C_4H_9$—t | $CH_3$ | |
| 4.108 | S | $CH_3$ | 2-$CH_3$ | 6-$CH_3$ | 4 | | $CF_3$ | $CH_3$ | |
| 4.109 | S | $CH_3$ | 2-$CH(CH_3)_2$ | H | 4 | | $C_2F_5$ | $CH(CH_3)_2$ | | where $Y = -N-$
                $|$
                $H$

| Comp. | X | $R_1$ | $R_4$ | $R_5$ | Position of $-OR_3$ | Y | $R_9$ | $R_{10}$ | m.p. [°C] |
|---|---|---|---|---|---|---|---|---|---|
| 4.110 | O | $CH_3$ | 2-$C_4H_9$—t | H | 4 | | $C_4H_9$—t | | |
| 4.111 | S | $CH_3$ | 2-$C_4H_9$—t | H | 4 | | $C_4H_9$—t | | |
| 4.112 | O | $CH_3$ | 2-$C_4H_9$—t | H | 4 | | cyclopropyl | | |
| 4.113 | S | $CH_3$ | 2-$C_4H_9$—t | H | 4 | | cyclopropyl | | |
| 4.114 | O | $CH_3$ | 4-$C_2H_5$ | H | 3 | | $C_4H_9$—t | | |
| 4.115 | S | $CH_3$ | 4-$C_2H_5$ | H | 3 | | $C_4H_9$—t | | |
| 4.116 | O | $CH_3$ | 4-$C_2H_5$ | H | 3 | | cyclopropyl | | |

**Al(III) salt

TABLE 5

Compounds of formula I, wherein $R_2$ is $CH_3$ and (Group If)

$-OR_3$ is  
$$-O-\overset{R_{11}}{\underset{5}{\overset{1}{N}}}-\overset{2}{\underset{4}{N}}-\overset{3}{\underset{R_9}{C}}$$

| Comp. | X | $R_1$ | $R_4$ | $R_5$ | Position of $-OR_3$ | $R_9$ | $R_{11}$ | m.p. [°C] |
|---|---|---|---|---|---|---|---|---|
| 5.1 | O | $CH_3$ | H | H | 4 | $CF_3$ | $CH_3$ | 202–204 |
| 5.2 | O | $CH_3$ | H | H | 4 | $CF_3$ | $CH(CH_3)_2$ | 202–203 |
| 5.3 | O | $CH_3$ | 2-$CH_3$ | 6-$CH_3$ | 4 | $CF_3$ | $CH_3$ | 158–160 |
| 5.4 | O | $CH_3$ | H | H | 4 | $C_2F_5$ | $CH_3$ | 173–174 |
| 5.5 | O | $CH_3$ | 2-$CH_3$ | 6-$CH_3$ | 4 | $CF_3$ | $CH(CH_3)_2$ | 198–199 |
| 5.6 | O | $CH_3$ | H | H | 4 | $C_2F_5$ | $CH(CH_3)_2$ | 152–153 |
| 5.7 | O | $CH_3$ | 2-$CH_3$ | 6-$CH_3$ | 4 | $C_2F_5$ | $CH(CH_3)_2$ | |
| 5.8 | O | $OCH_3$ | H | H | 4 | $CF_3$ | $CH_3$ | |
| 5.9 | O | $CH_3$ | 2-$CH_3$ | 6-$CH_3$ | 4 | $C_2F_5$ | $CH_3$ | 161–163 |

TABLE 5-continued

Compounds of formula I, wherein $R_2$ is $CH_3$ and $-OR_3$ is (Group If)

| Comp. | X | $R_1$ | $R_4$ | $R_5$ | Position of $-OR_3$ | $R_9$ | $R_{11}$ | m.p. [°C.] |
|---|---|---|---|---|---|---|---|---|
| 5.10 | O | $CH_3$ | 2-$CH(CH_3)_2$ | H | 4 | $CF_3$ | $CH_3$ | 246–248 |
| 5.11 | O | $CH_3$ | 2-$CH(CH_3)_2$ | H | 4 | $CF_3$ | $CH(CH_3)_2$ | 179–181 |
| 5.12 | S | $CH_3$ | H | H | 4 | $CF_3$ | $CH_3$ | 208–210 |
| 5.13 | S | $CH_3$ | H | H | 4 | $CF_3$ | $CH(CH_3)_2$ | 177–178 |
| 5.14 | S | $CH_3$ | 2-$CH_3$ | 6-$CH_3$ | 4 | $CF_3$ | $CH_3$ | |
| 5.15 | S | $CH_3$ | 2-$CH(CH_3)_2$ | H | 4 | $C_2F_5$ | $CH(CH_3)_2$ | 114–116 |
| 5.16 | O | $CH_3$ | H | H | 3 | $CF_3$ | $CH_3$ | 166–168 |
| 5.17 | O | $CH_3$ | H | H | 3 | $CF_3$ | $CH(CH_3)_2$ | |
| 5.18 | O | $OCH_3$ | H | H | 3 | $CF_3$ | $CH_3$ | |
| 5.19 | S | $CH_3$ | H | H | 3 | $CF_3$ | $CH_3$ | 194–195 |
| 5.20 | S | $CH_3$ | H | H | 3 | $CF_3$ | $CH(CH_3)_2$ | |
| 5.21 | S | $CH_3$ | 6-$CH_3$ | H | 3 | $CF_3$ | $CH_3$ | |
| 5.22 | S | $CH_3$ | 4-$CH_3$ | H | 3 | $CF_3$ | $CH_3$ | |
| 5.23 | O | $CH_3$ | 2-$CH(CH_3)_2$ | H | 3 | $CF_3$ | $CH_3$ | |
| 5.24 | O | $CH_3$ | 2-$CH(CH_3)_2$ | H | 3 | $CF_3$ | $CH(CH_3)_2$ | |
| 5.25 | O | $CH_3$ | 4-$CH_3$ | H | 3 | $CF_3$ | $CH(CH_3)_2$ | |
| 5.26 | O | $CH_3$ | H | H | 2 | $CF_3$ | $CH_3$ | |
| 5.27 | O | $CH_3$ | 4-$CH_3$ | H | 2 | $CF_3$ | $CH_3$ | |
| 5.28 | O | $CH_3$ | 2-$CH_3$ | 6-$CH_3$ | 4 | $C_3F_7$ | $CH_3$ | 167–169 |
| 5.29 | O | $CH_3$ | H | H | 3 | H | $CH_3$ | 202–204 |
| 5.30 | O | $CH_3$ | H | H | 4 | $CHCl_2$ | $CH_3$ | |
| 5.31 | O | $OCH_3$ | H | H | 4 | $NO_2$ | $CH_3$ | |
| 5.32 | O | $CH_3$ | H | H | 4 | $CCl_3$ | $CH_3$ | |
| 5.33 | O | $CH_3$ | H | H | 4 | $C_3H_7-n$ | $CH_3$ | |
| 5.34 | O | $CH_3$ | H | H | 3 | $C_3H_7-n$ | $CH_3$ | 149–151 |
| 5.35 | O | $CH_3$ | H | H | 4 | $C_3F_7-n$ | $CH_3$ | 177–179 |
| 5.36 | O | $CH_3$ | H | H | 3 | $C_2F_5$ | $CH(CH_3)_2$ | 123–124 |
| 5.37 | O | $CH_3$ | H | H | 3 | $C_2F_5$ | $CH_3$ | 146–147 |
| 5.38 | O | $OCH_3$ | H | H | 4 | $C_2F_5$ | $CH_3$ | 151–153 |
| 5.39 | O | $OCH_3$ | H | H | 3 | $C_2F_5$ | $CH_3$ | 138–140 |
| 5.40 | S | $CH_3$ | H | H | 4 | $C_2F_5$ | $CH_3$ | 149–150 |
| 5.41 | S | $C_2H_5$ | H | H | 4 | $CF_3$ | $CH_3$ | 185–186 |
| 5.42 | S | allyl | H | H | 4 | $CF_3$ | $CH_3$ | |
| 5.43 | S | $CH_3$ | H | H | 4 | $C_2F_5$ | $CH(CH_3)_2$ | 114–116 |
| 5.44 | S | $CH_3$ | H | H | 3 | $C_2F_5$ | $CH_3$ | 167–169 |
| 5.45 | O | allyl | H | H | 4 | $C_2F_5$ | $CH_3$ | |
| 5.46 | O | $C_2H_5$ | H | H | 4 | $CF_3$ | $CH(CH_3)_2$ | |
| 5.47 | S | allyl | H | H | 3 | $CF_3$ | $CH_3$ | 188–189 |
| 5.48 | O | allyl | H | H | 4 | $CF_3$ | $CH_3$ | 157–158 |
| 5.49 | O | $C_2H_5$ | H | H | 4 | $CF_3$ | $CH_3$ | 177–178 |
| 5.50 | O | $C_2H_5$ | H | H | 4 | $CF_3$ | $CH_3$ | 151–157 |

TABLE 6

Intermediates of formula III' (III')

| Comp. | $R_4$ | $R_5$ | Position of $-OR_3$ | $R_3$ | m.p. [°C.] |
|---|---|---|---|---|---|
| 6.1 | H | H | 4 | 5-tert-butyl-1,3,4-oxadiazol-2-yl | 80–81 |
| 6.2 | 2-$CH_3$ | 6-$CH_3$ | 4 | 1-isopropyl-3-trifluoromethyl-1H—1,2,4-triazol-5-yl | 153–155 |
| 6.3 | H | H | 4 | 5-tert-butyl-1,3,4-thiadiazol-2-yl | 81–83 |
| 6.4 | H | H | 4 | 6-chlorobenzothiazol-2-yl | 116–117 |
| 6.5 | H | H | 4 | 3-dichloromethyl-1,2,4-thiadiazol-5-yl | oil |
| 6.6 | H | H | 4 | 4-trifluoromethylthiazol-2-yl | 72 |
| 6.7 | H | H | 4 | Benzothiazol-2-yl | oil |
| 6.8 | 3-$CF_3$ | H | 4 | 5-tert-butyl-1,3,4-thiadiazol-2-yl | resin |
| 6.9 | H | H | 4 | benzoxazol-2-yl | |
| 6.10 | 2-$CH_3$ | 6-$CH_3$ | 4 | 1-methyl-3-trifluoromethyl-1H— | 155–156 |

TABLE 6-continued

Intermediates of formula III'

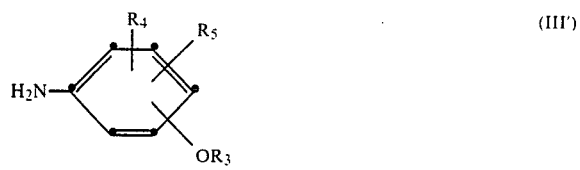

(III')

| Comp. | R₄ | R₅ | Position of —OR₃ | R₃ | m.p. [°C.] |
|---|---|---|---|---|---|
| 6.11 | 2-CH(CH₃)₂ | H | 4 | 1-isopropyl-3-trifluoromethyl-1H—1,2,4-triazol-5-yl | 107–109 |
| 6.12 | 2-CH(CH₃)₂ | H | 4 | 1-methyl-3-trifluoromethyl-1H—1,2,4-triazol-5-yl | 127–129 |
| 6.13 | H | H | 3 | 1-isopropyl-3-trifluoromethyl-1H—1,2,4-triazol-5-yl | resin |
| 6.14 | H | H | 3 | 1-methyl-1H—1,2,4-triazol-5-yl | resin |
| 6.15 | H | H | 4 | 1-isopropyl-3-trifluoromethyl-1H—1,2,4-triazol-5-yl | 138–139 |
| 6.16 | H | H | 3 | 1-methyl-3-trifluoromethyl-1H—1,2,4-triazol-5-yl | 109–110 |
| 6.17 | H | H | 3 | 5-tert-butyl-1,3,4-oxadiazol-2-yl | 83–84 |
| 6.18 | H | H | 4 | 5-tert-butyl-1,3,4-thiadiazol-2-yl | oil |
| 6.19 | H | H | 4 | 5-isopropyl-1,3,4-oxadiazol-2-yl | oil |
| 6.20 | H | H | 4 | 5-isopropyl-1,3,4-thiadiazol-2-yl | 93–94 |
| 6.21 | H | H | 3 | 5-isopropyl-1,3,4-thiadiazol-2-yl | resin |
| 6.22 | H | H | 3 | 5-tert-butyl-1,3,4-thiadiazol-2-yl | 104–105 |
| 6.23 | 2-CH₃ | H | 4 | 5-tert-butyl-1,3,4-thiadiazol-2-yl | 118–119 |
| 6.24 | H | H | 4 | 3-methylthio-1,2,4-thiadiazol-5-yl | semi-crystalline |
| 6.25 | H | 6-CH₃ | 3 | 3-trifluoromethyl-1,2,4-thiadiazol-5-yl | resin |
| 6.26 | H | H | 4 | 3-trichloromethyl-1,2,4-thiadiazol-5-yl | oil |
| 6.27 | H | H | 4 | 3-trifluoromethyl-1,2,4-thiadiazol-5-yl | 110–112 |
| 6.28 | 2-CH₃ | H | 4 | 4-trifluoromethylthiazol-2-yl | resin |
| 6.29 | H | H | 4 | 2,5-dichloro-1-methyl-1H—imidazol-4-yl | oil |
| 6.30 | H | H | 4 | 4-isopropyl-2-chloro-1H—1,2,4-triazol-3-yl | semi-crystalline |
| 6.31 | H | H | 4 | 3-chloro-1,2,4-thiadiazol-5-yl | oil |
| 6.32 | H | H | 4 | thiazol-2-yl | |
| 6.33 | H | H | 4 | 5-nitrothiazol-2-yl | semi-crystalline |
| 6.34 | H | H | 3 | 5-isobutyl-1,3,4-thiadiazol-2-yl | 93–94 |
| 6.35 | H | H | 4 | 5-cyclohexyl-1,3,4-thiadiazol-2-yl | |
| 6.36 | H | H | 4 | thiazol-2-yl | oil |
| 6.37 | H | H | 4 | thiazol-2-yl | oil |
| 6.38 | 2-CH₃ | H | 3 | benzothiazol-2-yl | oil |
| 6.39 | H | H | 3 | 4-nitrothiazol-2-yl | semi-crystalline |
| 6.40 | 6-CH₃ | H | 3 | 3-trifluoromethyl-1,2,4-thiadiazol-5-yl | oil |
| 6.41 | 2-CH₃ | H | 4 | 3-trifluoromethyl-1,2,4-thiadiazol-5-yl | 93–95 |
| 6.42 | H | H | 4 | 3-chloro-1,2,4-thiadiazol-5-yl | semi-crystalline |
| 6.43 | 2-CH₃ | H | 4 | 4-trifluoromethyl-thiazol-2-yl | resin |
| 6.44 | H | H | 4 | 4-trifluoromethyl-thiazol-2-yl | 72 |
| 6.45 | H | H | 3 | 6-chlorobenzothiazol-2-yl | oil |
| 6.46 | H | H | 4 | 6-bromobenzothiazol-2-yl | oil |
| 6.47 | 3-OCH₃ | H | 4 | 5-tert-butyl-1,3,4-thiadiazol-2-yl | semi-crystalline |
| 6.48 | 3-OCH₃ | H | 4 | 6-chlorobenzothiazol-2-yl | semi-crystalline |
| 6.49 | H | H | 4 | 6-fluorobenzothiazol-2-yl | oil |
| 6.50 | H | H | 4 | 6-trifluoromethylbenzothiazol-2-yl | oil |
| 6.51 | H | H | 4 | 1-methyl-3-trifluoromethyl-1H—1,2,4-triazol-5-yl | 111–112 |
| 6.52 | H | H | 4 | 1-methyl-3-pentafluoromethyl-1H—1,2,4-triazol-5-yl | 107–109 |
| 6.53 | H | H | 4 | 1-methyl-1H—1,2,4-triazol-5-yl | 127–128 |
| 6.54 | H | H | 4 | 1-isopropyl-3-pentafluoroethyl-1H—1,2,4-triazol-5-yl | 100–102 |
| 6.55 | CH₃ | CH₃ | 4 | 1-methyl-3-n-heptafluoropropyl-1H—1,2,4-triazol-5-yl | 130–133 |
| 6.56 | CH₃ | CH₃ | 4 | 1-methyl-3-pentafluoroethyl-1H—1,2,4-triazol-5-yl | 128 |
| 6.57 | H | H | 4 | 1-methyl-3-n-heptafluoropropyl-1H—1,2,4-triazol-5-yl | 65–67 |
| 6.58 | H | H | 3 | 1-methyl-3-n-heptafluoropropyl-1H—1,2,4-triazol-5-yl | 85–87 |
| 6.59 | H | H | 3 | 1-isopropyl-3-pentafluoroethyl-1H— | 88–90 |

TABLE 6-continued

Intermediates of formula III'

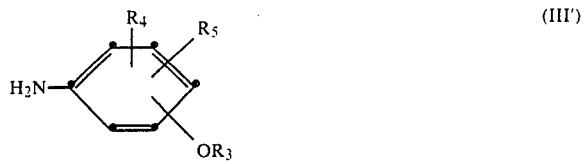

(III')

| Comp. | R_4 | R_5 | Position of —OR_3 | R_3 | m.p. [°C.] |
|---|---|---|---|---|---|
| 6.60 | H | H | 3 | 1,2,4-triazol-5-yl 1-methyl-3-pentafluoroethyl-1H—1,2,4-triazol-5-yl | 93–94 |
| 6.61 | CH_3 | CH_3 | 4 | 5-tert-butyl-1,3,4-oxadiazol-2-yl | 146–148 |
| 6.62 | H | H | 4 | 5-cyclopropyl-1,3,4-oxadiazol-2-yl | 75–77 |
| 6.63 | H | H | 4 | 5-cyclohexyl-1,3,4-oxadiazol-2-yl | 105–107 |
| 6.64 | (CH_3)_2CH | H | 4 | 5-cyclopropyl-1,3,4-oxadiazol-2-yl | oil |
| 6.65 | H | H | 4 | 5-(3-chlorophenyl)-1,3,4-oxadiazol-2-yl | 145–147 |
| 6.66 | H | H | 3 | 5-cyclopropyl-1,3,4-oxadiazol-2-yl | oil |
| 6.67 | H | H | 3 | 5-(3-chlorophenyl)-1,3,4-oxadiazol-2-yl | 82–84 |
| 6.68 | H | H | 3 | 5-isopropyl-1,3,4-oxadiazolyl-2-yl | oil |
| 6.69 | H | H | 3 | 5-cyclohexyl-1,3,4-oxadiazol-2-yl | 78–80 |
| 6.70 | H | H | 4 | 6-chlorobenzothiazol-2-yl | 116–117 |
| 6.71 | H | H | 4 | 6-fluoro-5-chlorobenzothiazol-2-yl | 147–149 |
| 6.72 | H | H | 4 | 6-fluoro-7-chlorobenzothiazol-2-yl | 156–157 |
| 6.73 | H | H | 4 | 6-methoxybenzothiazol-2-yl | oil |
| 6.74 | H | H | 4 | 6,7-dichlorobenzothiazol-2-yl | semi-crystalline |
| 6.75 | H | H | 4 | 5,6-dichlorobenzothiazol-2-yl | semi-crystalline |
| 6.76 | H | H | 4 | 4,7-difluorobenzothiazol-2-yl | oil |

Formulation Examples (throughout, percentages are by weight)

| F.1 Emulsifiable concentrates | (a) | (b) | (c) |
|---|---|---|---|
| a compound of the Tables | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of an required concentration can be produced from such concentrates by dilution with water.

| F.2 Solutions | (a) | (b) | (c) | (d) |
|---|---|---|---|---|
| a compound of the Tables | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| F.3 Granulates | (a) | (b) |
|---|---|---|
| a compound of the Tables | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo. Such granulates can be mixed with the cattle feed.

| F.4 Dusts | (a) | (b) |
|---|---|---|
| a compound of the Tables | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| F.5 Wettable powders | (a) | (b) | (c) |
|---|---|---|---|
| a compound of the Tables | 25% | 50% | 75% |
| sodium lignosulfonate | 5% | 5% | — |
| oleic acid | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| F.6 Emulsifiable concentrate | (a) | (b) | (c) |
|---|---|---|---|
| a compound of the Tables | 10% | 8% | 60% |
| octylphenol polyethylene glycol ether (4–5 moles of ethylene oxide) | 3% | 3% | 2% |
| castor oil polyglcol ether (35 moles of ethylene oxide) | 4% | 5% | 4% |
| cyclohexanone | 30% | 40% | 15% |
| xylene mixture | 50% | 40% | 15% |

Emulsions of any required concentration can be obtained from this concentrate by dilution with water.

| F.7 Dust | (a) | (b) |
|---|---|---|
| a compound of the Tables | 5% | 8% |
| talcum | 95% | — |
| kaolin | — | 92% |

Ready-for-use dusts are obtained by mixing the active ingredient with the carrier, and grinding the mixture in a suitable mill.

| F.8 Granulate | |
|---|---|
| a compound of the Tables | 10% |
| sodium lignosulfonate | 2% |
| carboxymethylcellulsoe | 1% |
| kaolin | 87% |

The active ingredient is mixed and ground with the adjuvants, and the mixture is subsequently moistened with water. The mixture is extruded and then dried in a stream of air.

| F.9 Granulate | |
|---|---|
| a compound of the Tables | 3% |
| polyethlene glycol 200 | 3% |
| kaolin | 94% |

The finely ground active ingredient is uniformly applied, in a mixer, to the kaolin moistened with polyethylene glycol. Non-dusty coated granulates are obtained in this manner.

| F.10 Suspension concentrate | |
|---|---|
| a compound of the Tables | 40% |
| ethylene glycol | 10% |
| nonylphenol polyethylene glycol (15 moles of ethlene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

| F.11 Tablets or boluses | |
|---|---|
| I M compound of the Tables | 33.0% |
| methyl cellulose | 0.80% |
| highly dispersed silic acid | 0.80% |
| maize starch | 8.40% |
| II crystalline lactose | 22.50% |
| maize starch | 17.00% |
| microcrystalline cellulose | 16.50% |
| magnesium stearate | 1.00% |

I The methyl cellulose is stirred in water and allowed to swell. Then the silicic acid is stirred in to give a homogeneous suspension. The compound of formula I and the maize starch are mixed and the aqueous suspension is added to the mix, which is kneaded to a paste. This paste is granulated through a 12 M sieve and the granulate is dried.
II All 4 adjuvants are thoroughly mixed.
III Phases I and II are mixed and compressed to tablets or

| F.11 Tablets or boluses |
|---|
| boluses. |

BIOLOGICAL EXAMPLE

The following test procedure is employed to demonstrate the anthelmintic activity of the compounds of formula I:

B.1. Trial with sheep infected with nematodes such as *Haemonchus concortus* and *Trichostrongylus colubriformis*

The test compound is administered in the form of a suspension with a stomach probe or by intrarumenal injection to sheep which have been artificially infected beforehand with nematodes such as *Haemonchus concortus* and *Trichostrongylus colubriformis*. One to three animals are used for each trial and for each dose. Each sheep is treated with only a single dose. A first evaluation is made by comparing the number of worm eggs excreted in the faeces of the sheep before and after treatment. The sheep are slaughtered and dissected 7 to 10 days after treatment. Evaluation is made by counting the number of worms remaining in the intestine after treatment. Untreated sheep infected simultaneously and in the same manner are used as controls.

Compared with the untreated and infected control groups, nematode infestation is reduced by at least 90% in sheep which are treated with a suspension formulation of a compound of Table 1 applied at a dose of 20 mg/kg of body weight. Moreover, compounds 1.1, 1.4, 1.5, 1.6, 1.8, 1.9, 1.11, 1.32, 1.33, 1.38, 1.39, 1.41, 1.43, 1.53, 1.54, 1.55, 1.57, 1.63, 1.78, 1.79, 1.80, 3.1, 4.1, 4.2, 4.3, 4.10, 4.20, 4.54, 4.55, 4.59, 4.66, 5.1, 5.2, 5.3, 5.4, 5.5, 5.6, 5.16, 5.28, 5.29 und 5.37 are at least 95% effective when applied at a dose of 10 mg/kg.

What is claimed is:

1. A compound of the formula $$X = \begin{pmatrix} R_1 \\ N \\ \\ N \\ R_2 \end{pmatrix} \begin{matrix} O \\ \\ O \end{matrix} - C - N - \begin{pmatrix} R_4 & R_5 \\ \\ \\ \\ O-R_3 \end{pmatrix}$$

wherein
X is oxygen or sulfur;
$R_1$ is $C_1$-$C_6$alkyl, $C_1$-$C_6$alkoxy, $C_3$-$C_6$cycloalkyl or allyl;
$R_2$ is $C_1$-$C_6$ alkyl or allyl;
$R_3$ is a five-membered azole ring unsubstituted or substituted by one or two halogen or nitro groups or by alkyl, haloalkyl, alkoxy or alkylthio groups each of which alkyl-containing groups has 1 to 6 carbon atoms $C_3$-$C_7$cycloalkyl and which is bound through carbon and is selected from the group consisting of benzimidazole, benzoxazole, benzothiazole, imidazole, oxazole, thiazole, oxadiazole, thiadiazole and triazole; and
$R_4$ and $R_5$ are independently of the other hydrogen, $C_1$-$C_6$alkyl, $C_1$-$C_6$haloalkyl, $C_1$-$C_6$alkoxy or $C_1$-$C_6$haloalkoxy;
or a tautomer or salt thereof.

2. A compound according to claim 1, wherein X is oxygen or sulfur; $R_1$ is $C_1$-$C_6$alkyl, $C_1$-$C_6$alkoxy, $C_3$-$C_6$cycloalkyl or allyl; $R_2$ is $C_1$-$C_6$alkyl or allyl; each of $R_4$ and $R_5$ independently of the other is hydrogen, $C_1$-$C_6$alkyl, $C_1$-$C_6$alkoxy or $C_1$-$C_6$haloalkoxy; and $R_3$ is a group selected from the series consisting of

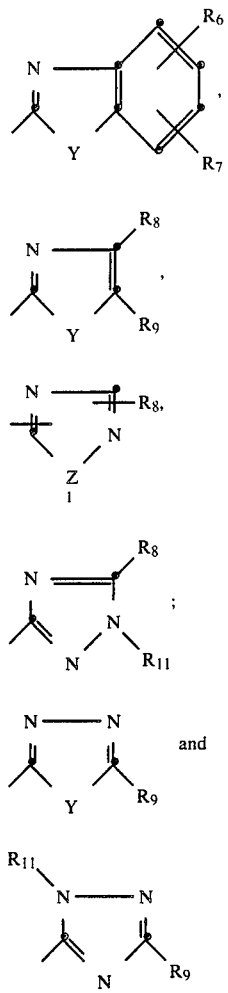

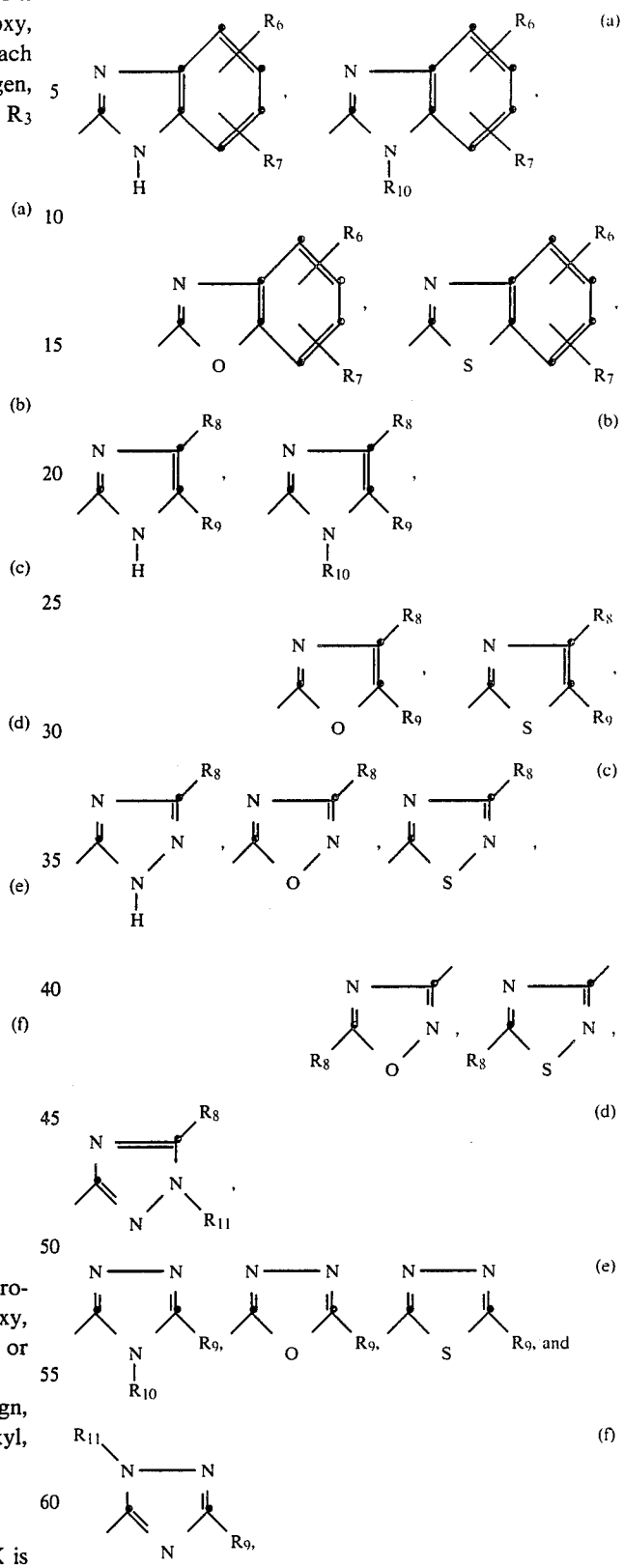

in which formulae
Y is oxygen, sulfur or $NR_{10}$;
$Z_1$ is oxygen, sulfur or NH;
$R_6$ and $R_7$ are each independently of the other hydrogen, $C_1$-$C_4$alkyl, $C_1$-$C_4$haloalkyl, $C_1$-$C_4$alkoxy, $C_1$-$C_4$haloalkoxy, $C_1$-$C_4$alkylthio, halogen, nitro or cyano;
$R_8$ and $R_9$ are each independently of the other hydrogn, $C_1$-$C_6$alkyl, $C_3$-$C_7$cycloalkyl, $C_1$-$C_6$haloalkyl, $C_1$-$C_6$alkoxy, $C_1$-$C_6$alkylthio, halogen or nitro;
$R_{10}$ is hydrogen or $C_1$-$C_6$alkyl; and
$R_{11}$ is $C_1$-$C_6$alkyl.

3. A compound according to claim 2, wherein X is oxygen or sulfur; $R_1$ is $C_1$-$C_6$alkyl, $C_1$-$C_6$alkoxy, $C_3$-$C_6$cycloalkyl or allyl; $R_2$ is $C_1$-$C_6$alkyl or allyl; each of $R_4$ and $R_5$ independently of the other is hydrogen, $C_1$-$C_6$alkyl, $C_1$-$C_6$alkoxy or $C_1$-$C_6$haloalkoxy; and $R_3$ is a group selected from the series consisting of in which formulae
$R_6$ and $R_7$ are each independently of the other hydrogen, $C_1$-$C_4$alkyl, $C_1$-$C_4$haloalkyl, $C_1$-$C_4$alkoxy, $C_1$-$C_4$haloalkoxy, $C_1$-$C_4$alkylthio, halogen, nitro or cyano;

$R_8$ and $R_9$ are each independently of the other hydrogen, $C_1$-$C_6$alkyl, $C_1$-$C_6$haloalkyl, $C_1$-$C_6$alkoxy, $C_1$-$C_6$alkylthio, halogen or nitro;
$R_{10}$ is hydrogen or $C_1$-$C_6$alkyl; and
$R_{11}$ is $C_1$-$C_6$alkyl.

4. A compound according to claim 2, wherein X is oxygen or sulfur; $R_1$ is $C_1$-$C_6$alkyl, $C_1$-$C_6$alkoxy, $C_3$-$C_6$cycloalkyl or allyl; $R_2$ is $C_1$-$C_6$alkyl or allyl; each of $R_4$ and $R_5$ independently of the other is hydrogen, $C_1$-$C_6$alkyl, $C_1$-$C_6$alkoxy or $C_1$-$C_6$haloalkoxy; and $R_3$ is the group

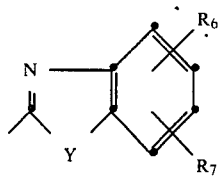 (a)

wherein each of $R_6$ and $R_7$ independently of the other is hydrogen, $C_1$-$C_4$alkyl, $C_1$-$C_4$haloalkyl, $C_1$-$C_4$alkoxy, $C_1$-$C_4$haloalkoxy, $C_1$-$C_4$-alkylthio, halogen, nitro or cyano; and Y is oxygen, sulfur or $NR_{10}$, wherein $R_{10}$ is hydrogen or $C_1$-$C_6$alkyl.

5. A compound according to claim 2, wherein X is oxygen or sulfur; $R_1$ is $C_1$-$C_6$ alkyl, $C_1$-$C_6$ alkoxy, $C_3$-$C_6$ cycloalkyl or allyl; $R_2$ is $C_1$-$C_6$ alkyl or allyl; each of $R_4$ and $R_5$ independently of the other is hydrogen, $C_1$-$C_6$ alkyl, $C_1$-$C_6$ alkoxy or $C_1$-$C_6$ haloalkoxy; and $R_3$ is the group of

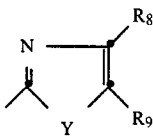 (b)

wherein each of $R_8$ and $R_9$ independently of the other is hydrogen, $C_1$-$C_6$ alkyl, $C_3$-$C_7$ cycloalkyl, $C_3$-$C_7$ cycloalkyl substituted by halogen or $C_1$-$C_3$ alkyl, $C_1$-$C_6$ haloalkyl, $C_1$-$C_6$ alkoxy, $C_1$-$C_6$ alkylthio, halogen or nitro; and Y is oxygen, sulfur or $NR_{10}$, wherein $R_{10}$ is hydrogen or $C_1$-$C_6$ alkyl.

6. A compound according to claim 2, wherein X is oxygen or sulfur; $R_1$ is $C_1$-$C_6$alkyl, $C_1$-$C_6$alkoxy, $C_3$-$C_6$cycloalkyl or allyl; $R_2$ is $C_1$-$C_6$alkyl or allyl; each of $R_4$ and $R_5$ independently of the other is hydrogen, $C_1$-$C_6$alkyl, $C_1$-$C_6$alkoxy or $C_1$-$C_6$haloalkoxy; and $R_3$ is the group

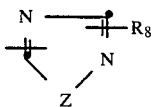 (c)

wherein $R_8$ is hydrogen, $C_1$-$C_6$alkyl, $C_1$-$C_6$haloalkyl, $C_1$-$C_6$alkoxy, $C_1$-$C_6$alkylthio, halogen or nitro; and Z is oxygen, sulfur or NH.

7. A compound according to claim 2, wherein X is oxygen or sulfur; $R_1$ is $C_1$-$C_6$alkyl, $C_1$-$C_6$alkoxy, $C_3$-$C_6$cycloalkyl or allyl; $R_2$ is $C_1$-$C_6$alkyl or allyl; each of $R_4$ and $R_5$ independently of the other is hydrogen, $C_1$-$C_6$alkyl, $C_1$-$C_6$alkoxy or $C_1$-$C_6$haloalkoxy; and $R_3$ is the group

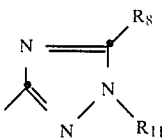 (d)

wherein $R_8$ is hydrogen, $C_1$-$C_6$alkyl, $C_1$-$C_6$haloalkyl, $C_1$-$C_6$alkoxy, $C_1$-$C_6$alkylthio, halogen or nitro; and $R_{11}$ is $C_1$-$C_6$alkyl.

8. A compound according to claim 2, wherein X is oxygen or sulfur; $R_1$ is $C_1$-$C_6$alkyl, $C_1$-$C_6$alkoxy, $C_3$-$C_6$cycloalkyl or allyl; $R_2$ is $C_1$-$C_6$alkyl or allyl; each of $R_4$ and $R_5$ independently of the other is hydrogen, $C_1$-$C_6$alkyl, $C_1$-$C_6$alkoxy or $C_1$-$C_6$haloalkoxy; and $R_3$ is the group

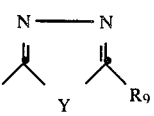 (e)

wherein $R_9$ is hydrogen, $C_1$-$C_6$alkyl, $C_1$-$C_6$haloalkyl, $C_1$-$C_6$alkoxy, $C_1$-$C_6$alkylthio, halogen or nitro; and Y is oxygen, sulfur or $NR_{10}$, wherein $R_{10}$ is hydrogen or $C_1$-$C_6$alkyl.

9. A compound according to claim 1, wherein X is oxygen or sulfur; $R_1$ is $C_1$-$C_6$alkyl, $C_1$-$C_6$alkoxy, $C_3$-$C_6$cycloalkyl or allyl; $R_2$ is $C_1$-$C_6$alkyl or allyl; each of $R_4$ and $R_5$ independently of the other is hydrogen, $C_1$-$C_6$alkyl, $C_1$-$C_6$alkoxy or $C_1$-$C_6$haloalkoxy; and $R_3$ is a group selected from the series consisting of

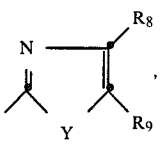 (b)

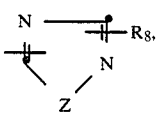 (c)

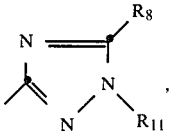 (d)

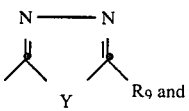 (e)

$R_9$ and

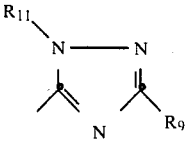 (f)

in which formulae each of $R_8$ and $R_9$ independently of the other is $C_3$-$C_7$cycloalkyl which is unsubstituted or substituted by halogen or $C_1$-$C_3$alkyl; Y is oxygen, sulfur or NR₁₀; Z is hydrogen, sulfur or NH; R₁₀ is hydrogen or C₁-C₆alkyl; and R₁₁ is C₁-C₆alkyl.

10. A compound according to claim 2, wherein X is oxygen or sulfur; R₁ is C₁-C₆alkyl, C₁-C₆alkoxy, C₃-C₆cycloalkyl or allyl; R₂ is C₁-C₆alkyl or allyl; each of R₄ and R₅ independently of the other is hydrogen, C₁-C₆alkyl, C₁-C₆alkoxy or C₁-C₆haloalkoxy; and R₃ is the group

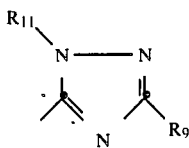  (f)

wherein R₉ is hydrogen, C₁-C₆alkyl, C₁-C₆haloalkyl, C₁-C₆alkoxy, C₁-C₆alkylthio, halogen or nitro; and R₁₁ is C₁-C₆alkyl.

11. A compound according to claim 2, wherein X is oxygen or sulfur; R₁ is C₁-C₆alkyl, C₁-C₆alkoxy, C₃-C₆cycloalkyl or allyl; R₂ is C₁-C₆alkyl or allyl; each of R₄ and R₅ independently of the other is hydrogen, C₁-C₆alkyl, C₁-C₆alkoxy or C₁-C₆haloalkoxy; and R₃ is the group

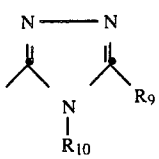  (e)

wherein R₉ is hydrogen, C₁-C₆alkyl, C₃-C₇cycloalkyl, C₁-C₆haloalkyl, C₁-C₆alkoxy, C₁-C₆alkylthio, halogen or nitro; and R₁₀ is hydrogen or C₁-C₆alkyl.

12. A compound according to claim 1, wherein X is oxygen or sulfur; R₁ is methyl or methoxy; R₂ is methyl; each of R₄ and R₅ independently of the other is hydrogen, methyl, CF₃, OCH₃, OCHF₂ or OCF₃.

13. A compound according to claim 4, wherein each of R₆ and R₇ independently of the other is hydrogen, methyl, CF₃, methoxy, halomethoxy, fluorine, chloride or bromine; and the remaining substituents are as defined in any one of claims 1 to 11.

14. A compound according to claim 5, wherein each of R₈ and R₉ independently of the other is hydrogen, methyl, ethyl, C₃-C₇ cycloalkyl, CF₃, C₂F₅, C₃F₇, CCl₃, CHCl₂, CH₂Cl, SCH₃ or halogen.

15. A compound according to claim 10 wherein R₉ is hydrogen, methyl, ethyl, C₃-C₇ cycloalkyl, CF₃, C₂F₅, C₃F₇, CCl₃, CHCl₂, CH₂Cl, SCH₃ or halogen, and R₁₁ is C₁-C₄ alkyl.

16. A compound according to claim 11 wherein R₉ is hydrogen, methyl, ethyl, C₃-C₇ cycloalkyl, CF₃, C₂F₅, C₃F₇, CCl₃, CHCl₂, CH₂Cl, SCH₃ or halogen and R₁₀ is hydrogen or methyl.

17. A compound according to claim 1, selected from the series consisting of
1,3-dimethyl-5-[4-(6-bromobenzothiazol-2-yloxy)-phenylcarbamoyl]barbituric acid;
1,3-dimethyl-5-[4-(6-chlorobenzothiazol-2-yloxy)-phenylcarbamoyl]barbituric acid;
1,3-dimethyl-5-[4-(6-fluoro(benzothiazol-2-yloxy)-phenylcarbamoyl]barbituric acid;
1,3-dimethyl-5-[4-(3-dichloromethyl-1,2,4-thiadiazol-5-yloxy)phenylcarbamoyl]barbituric acid;
1,3-dimethyl-5-[4-(5-tert-butyl-1,3,4-oxadiazol-2-yloxy)phenylcarbamoyl]barbituric acid;
1,3-dimethyl-5-[4-(5-tert-butyl-1,3,4-thiadizol-2-yloxy)-phenylcarbamoyl]barbituric acid;
1-methyl-3-methoxy-5-[4-(5-tert-butyl-1,3,4-thiadiazol-2-yloxy)phenylcarbamoyl]barbituric acid;
1,3-dimethyl-5-[4-(5-isopropyl-1,3,4-oxadiazol-2-yloxy)phenylcarbamoyl]barbituric acid;
1,3-dimethyl-5-[4-(1-isopropyl-3-trifluoromethyl-1H-1,2,4-triazol-5-yloxy)phenylcarbamoyl]barbituric acid;
1,3-dimethyl-5-[2,6-dimethyl-4-(1-methyl-3-heptafluoropropyl-1H-1,2,4-triazol-5-yloxy)phenylcarbamoyl]barbituric acid;
1,3-dimethyl-5-[4-(1-isopropyl-3-pentafluoroethyl-1H-1,2,4-triazol-5-yloxy)phenylcarbamoyl]barbituric acid;
1,3-dimethyl-5-[4-(1-isopropyl-3-trifluoromethyl-1H-1,2,4-triazol-5-yloxy)-2,6-dimethylphenylcarbamoyl]-barbituric acid;
1,3-dimethyl-5-[3-(1-methyl-3-trifluoromethyl-1H-1,2,4-triazol-5-yloxy)phenylcarbamoyl]barbituric acid;
1,3-dimethyl-5-[4-(6-trifluoromethylbenzothiazol-2-yloxy)phenylcarbamoyl]barbituric acid;
1,3-dimethyl-5-[3-methoxy-4-(5-tert-butyl-1,3,4-thiadiazol-2-yloxy)phenylcarbamoyl]barbituric acid;
1,3-dimethyl-5-[3-methoxy-4-(6-chlorobenzothiazol-2-yloxy)phenylcarbamoyl]barbituric acid;
1,3-dimethyl-5-[4-(5,6-dichlorobenzothiazol-2-yloxy)-phenylcarbamoyl]barbituric acid;
1,3-dimethyl-5-[4-(6,7-dichlorobenzothiazol-2-yloxy)-phenylcarbamoyl]barbituric acid;
1,3-dimethyl-5-[4-(benzothiazol-2-yloxy)phenylcarbamoyl]barbituric acid;
1,3-dimethyl-5-[4-(5-chloro-6-fluorobenzothiazol-2-yloxy)phenylcarbamoyl]barbituric acid;
1,3-dimethyl-5-[4-(7-chloro-6-fluorobenzothiazol-2-yloxy)phenylcarbamoyl]barbituric acid;
1,3-dimethyl-5-[4-(6-trifluoromethoxybenzothiazol-2-yloxy)phenylcarbamoyl]barbituric acid;
1,3-dimethyl-5-[2-isopropyl-4-(5-cyclopropyl-1,3,4-oxadiazol-2-yloxy)phenylcarbamoyl]barbituric acid;
1,3-dimethyl-5-[4-(5-cyclohexyl-1,3,4-thiadiazol-2-yloxy)phenylcarbamoyl]barbituric acid;
1,3-dimethyl-5-[4-(1-methyl-3-pentafluoroethyl-1H-1,2,4-triazol-5-yloxy)phenylcarbamoyl]barbituric acid;
1,3-dimethyl-5-[4-(6-methoxybenzothiazol-2-yloxy)-phenylcarbamoyl]barbituric acid;
1,3-dimethyl-5-[4-(5-cyclopropyl-1,3,4-thiadiazol-2-·yloxy)phenylcarbamoyl]barbituric acid;
1,3-Dimethyl-5-[4-(6-chloro-7-fluorobenzothiazol-2-yloxy)phenylcarbamoyl]barbituric acid;
1-methyl-3-methoxy-5-[4-(6-chloro-7-fluorobenzothiazol-2-yloxy)phenylcarbamoyl]barbituric acid and
1,3-dimethyl-5-[3-methoxy-4-(6-chloro-7-fluorobenzothiazol-2-yloxy)phenylcarbamoyl]barbituric acid.

18. An anthelmintic composition which contains, as the active ingredient, at least one compound of the formula

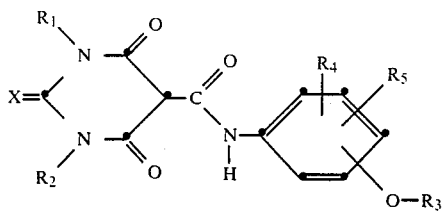

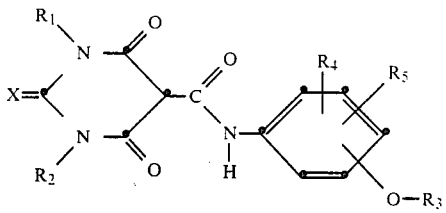

wherein

X is oxygen or sulfur;

$R_1$ is $C_1$–$C_6$alkyl, $C_1$–$C_6$alkoxy, $C_3$–$C_6$cycloalkyl or allyl;

$R_2$ is $C_1$–$C_6$alkyl or allyl;

$R_3$ is a five-membered azole ring unsubstituted or substituted by one or two halogen or nitro groups or by alkyl, haloalkyl, alkoxy or alkylthio groups each of which alkyl-containing groups has 1 to 6 carbon atoms $C_3$–$C_7$ cycloalkyl and which is bound through carbon and is selected from the group consisting of benzimidazole, benzoxazole, benzothiazole, imidazole, oxazole, thiazole, oxadiazole, thiadiazole and triazole; and $R_4$ and $R_5$ are independently of the other hydrogen, $C_1$–$C_6$alkyl, $C_1$–$C_6$haloalkyl, $C_1$–$C_6$alkoxy or $C_1$–$C_6$haloalkoxy;

or a tautomer or salt thereof.

19. A composition according to claim 18, which composition contains 0.1 to 99.0% by weight of said compound and 99.9 to 1% by weight of carriers and further assistants.

20. A method of controlling parasitic helminths, which method comprises administering to an animal an anthelmintically effective amount of a compound of the formula wherein X is oxygen or sulfur;

$R_1$ is $C_1$–$C_6$alkyl, $C_1$–$C_6$alkoxy, $C_3$–$C_6$cycloalkyl or allyl;

$R_2$ is $C_1$–$C_6$alkyl or allyl;

$R_3$ is five-membered azole ring unsubstituted or substituted by one or two halogen or nitro groups or by alkyl, haloalkyl, alkoxy or alkylthio groups each of which alkyl-containing groups has 1 to 6 carbon atoms $C_3$–$C_7$ cycloalkyl and which is bound through carbon and is selected from the group consisting of benzimidazole, benzoxazole, benzothiazole, imidazole, oxazole, thiazole, oxadiazole, thiadiazole and triazole; and $R_4$ and $R_5$ are independently of the other hydrogen, $C_1$–$C_6$alkyl, $C_1$–$C_6$haloalkyl, $C_1$–$C_6$alkoxy or $C_1$–$C_6$haloalkoxy;

or a tautomer or salt thereof.

21. A method of controlling parasitic helminths, which comprises administering to an animal an anthelmintically effective amount of a compound of claim 2.

22. A compound of the formula

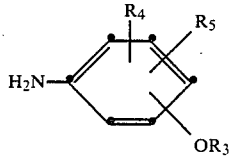

wherein $R_4$, $R_5$ and $R_3$ are as defined in claim 1.

* * * * *